US012746015B2

(12) United States Patent
Woollen

(10) Patent No.: US 12,746,015 B2
(45) Date of Patent: Sep. 29, 2026

(54) MOUNTING SYSTEMS

(71) Applicant: DEPUY IRELAND UNLIMITED COMPANY, Ringaskiddy (IE)

(72) Inventor: Neil Woollen, Bradford (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 20 days.

(21) Appl. No.: 18/728,536

(22) PCT Filed: Feb. 8, 2023

(86) PCT No.: PCT/EP2023/053089
§ 371 (c)(1),
(2) Date: Jul. 12, 2024

(87) PCT Pub. No.: WO2023/152172
PCT Pub. Date: Aug. 17, 2023

(65) Prior Publication Data

US 2025/0072906 A1 Mar. 6, 2025

(30) Foreign Application Priority Data

Feb. 8, 2022 (GB) ..................................... 2201569

(51) Int. Cl.
*A61B 17/16* (2006.01)

(52) U.S. Cl.
CPC .................................. *A61B 17/162* (2013.01)

(58) Field of Classification Search
CPC .............. A61B 17/162; A61B 17/1659; A61B 17/1668; A61F 2/4607
See application file for complete search history.

(56) References Cited

U.S. PATENT DOCUMENTS 3,874,383 A 4/1975 Glowacki
5,472,415 A 12/1995 King et al.
(Continued)

FOREIGN PATENT DOCUMENTS

EP 2047826 A1 4/2009
FR 2676172 A1 11/1992
(Continued)

OTHER PUBLICATIONS

International Search Report for Corresponding PCT Application No. PCT/EP2023/053089 Dated Apr. 18, 2023, 2 Pages.
(Continued)

*Primary Examiner* — Eduardo C Robert
*Assistant Examiner* — Holly Joanna Lane
(74) *Attorney, Agent, or Firm* — Barnes & Thornburg LLP

(57) ABSTRACT

A mounting component, kit incorporating the same and method of use are provided, for connecting a surgical procedural element to another element, with improved case of use. The mounting component comprising: a mount body provided at an end of the another element or at the end of the surgical procedural element; wherein: the mount body has a first end and a second end, the mount body has a longitudinal axis, the first end being spaced from the second end along the longitudinal axis, the mount body has a first surface profile section, the first surface profile section including a first radial profile considered perpendicular to the longitudinal axis; the mount body has a second surface profile section, the second surface profile section being closer to the second end of the mount body than the first surface profile section, the second surface profile section including a second radial profile considered perpendicular to the longitudinal axis and parallel to the first radial profile; wherein the second surface profile section is at least partially defined by
(Continued)

one or more alignment elements and the second radial profile has a different radial profile to the first radial profile surface due to the presence of the one or more alignment elements.

15 Claims, 13 Drawing Sheets

(56) References Cited

U.S. PATENT DOCUMENTS

| | | | | |
|---|---|---|---|---|
| 7,001,391 | B2 | 2/2006 | Estes | |
| 8,419,760 | B2 | 4/2013 | Belagali | |
| 10,159,495 | B1 * | 12/2018 | Lambert | A61B 17/1615 |
| 10,405,991 | B2 | 9/2019 | Bailey | |
| 10,709,508 | B2 * | 7/2020 | Barnes | A61B 17/1622 |
| 11,076,871 | B2 | 8/2021 | Barnes | |
| 11,517,328 | B2 * | 12/2022 | Adams | A61M 1/76 |
| 2002/0177854 | A1 | 11/2002 | Tuke et al. | |
| 2003/0023256 | A1 * | 1/2003 | Estes | A61B 17/1633 606/167 |
| 2003/0163134 | A1 | 8/2003 | Riedel | |
| 2006/0058885 | A1 | 3/2006 | Wozencroft | |
| 2006/0281048 | A1 * | 12/2006 | Bailey | B25G 1/005 433/165 |
| 2008/0269765 | A1 | 10/2008 | Banerjee et al. | |
| 2009/0099566 | A1 | 4/2009 | Maness et al. | |
| 2009/0261536 | A1 * | 10/2009 | Beale | B23B 31/1071 279/19.7 |
| 2012/0184964 | A1 | 7/2012 | Hudak, Jr. et al. | |
| 2012/0253323 | A1 * | 10/2012 | Bharadwaj | A61B 17/8883 606/1 |
| 2012/0259337 | A1 * | 10/2012 | del Rio | A61B 17/1617 29/428 |
| 2012/0290099 | A1 | 11/2012 | Gibson et al. | |
| 2013/0023934 | A1 | 1/2013 | Haas | |
| 2013/0245629 | A1 * | 9/2013 | Xie | A61B 17/1624 606/80 |
| 2016/0206327 | A1 | 7/2016 | Wiebe, III | |
| 2016/0331551 | A1 | 11/2016 | Slade et al. | |
| 2018/0055519 | A1 | 3/2018 | Barnes | |
| 2019/0336307 | A1 | 11/2019 | Sungo et al. | |

FOREIGN PATENT DOCUMENTS

| | | | |
|---|---|---|---|
| WO | 9515133 | A1 | 6/1995 |
| WO | 2007002230 | A1 | 1/2007 |
| WO | 2010006084 | A2 | 1/2010 |
| WO | 20200161511 | A1 | 8/2020 |

OTHER PUBLICATIONS

GB Search Report for Corresponding Application No. 2201569.7, 1 Page.

International Search Report for Corresponding PCT App. No. PCT/EP2023/059407 dated Jun. 7, 2023, 15 pages.

GB Search Report for Corresponding GB Patent App. No. GB2205303.7 dated Sep. 27, 2022, 4 pages.

International Examination Report for Corresponding EP App. No. 23719339.6-1122 dated Dec. 12, 2025, 7 pages.

Single Use Medical Devices, MRHA Leaflet (Dec. 2013), 1 Page, https://www.gov.uk/government/publications/single-use-medical-devices-leaflet.

* cited by examiner

MOUNTING SYSTEMS

CROSS-REFERENCE TO RELATED APPLICATIONS

This application is a national stage entry under 35 U.S.C. § 371(b) of PCT International Application No. PCT/EP2023/053089 filed Feb. 8, 2023, which claims priority to Great Britain Patent Application No. 2201569.7 filed on Feb. 8, 2022, now abandoned, both of which are incorporated herein by reference in their entireties.

TECHNICAL FIELD

This disclosure concerns improvements in and relating to mounting systems, particularly for surgical procedural elements, including those using in orthopaedic surgery.

BACKGROUND

It is amongst the potential but non-limiting aims of the present disclosure to provide a mounting system capable of readily aligning its components when connecting to one another, for instance before transferring high levels, primarily torque, but also axial loading [compressive and tensile] to a surgical procedural element, such as a reamer. It is amongst the potential but non-limiting aims of the present disclosure to provide a mounting system which is self-aligning in a rotational sense.

SUMMARY

According to a first aspect of the disclosure there is provided a mounting component for connecting a surgical procedural element to another element, the mounting component comprising:

- a mount body provided at an end of the another element or at the end of the surgical procedural element; wherein:
  - the mount body has a first end and a second end, the mount body has a longitudinal axis, the first end being spaced from the second end along the longitudinal axis,
  - the mount body has a first surface profile section, the first surface profile section including a first radial profile considered perpendicular to the longitudinal axis;
  - the mount body has a second surface profile section, the second surface profile section being closer to the second end of the mount body than the first surface profile section, the second surface profile section including a second radial profile considered perpendicular to the longitudinal axis and parallel to the first radial profile;

wherein the second surface profile section is at least partially defined by one or more alignment elements and the second radial profile has a different radial profile to the first radial profile surface due to the presence of the one or more alignment elements.

The mounting component may be provided on the another element. The another element may be a force applicator, such as a motive power source, or an extension element. A second mounting component may be provided on a surgical procedural element in that case, potentially according to the second aspect of the disclosure. The one or more or all, of the surgical procedural elements may be surgical instruments for instance. The one or more surgical procedural elements may be reamers and/or rasps and/or broaches. The one or more surgical procedural elements may be surgical components, such as trial components and/or final components for the surgical procedure.

The mounting component may be provided on the surgical procedural element. A second mounting component may be provided on the another element in that case, potentially according to the second aspect of the disclosure.

The mounting component may be a female component, in a first embodiment, with the second component a male component. The female component may be provided on the another element.

The mounting component may be a male component, in a further embodiment, with the second component a female component. The male component may be provided on the surgical procedural element.

Where the mounting component is a female component, a first embodiment, the second surface profile section may have a different radial profile to the first radial profile surface due to the presence of the one or more alignment elements and the one or more alignment elements reducing the second radial profile in those parts of the second radial profile for which they are present. The one or more alignment elements may extend radially inward. The one or more alignment elements may extend radially inward into a bore in the mount body.

Where the mounting component is a male component, a further embodiment, the second surface profile section may have a different radial profile to the first radial profile surface due to the presence of the one or more alignment elements and the one or more alignment elements increasing the second radial profile in those parts of the second radial profile for which they are present. The one or more alignment elements may extend radially outward. The one or more alignment elements may extend radially outward away from an external surface of the mount body.

The mount body may include an external wall. The external wall may at least partially enclose an internal bore. The external wall may define an external surface profile section for the mount body. The external surface profile section may be at least partially cylindrical. The external surface profile section may include two or more partially cylindrical profile parts, for instance with intermediate profile parts between them. The external surface profile section may include two or more planar profile parts. One or more or all, of the intermediate profile parts may be provided by planar profile parts. The external surface profile section may be defined in part by alternating planar profile parts and partially cylindrical profile parts.

One or more external profile parts, for instance one or more or all, of the planar profile parts, may, in use, provide for the application of torque to the mount body.

One or more through apertures may be provided in the mount body. For instance, a through aperture may be provided in one or more of the planar profile parts. The one or more through apertures may be provided in a third surface of the mount body. One or more parts of the other of the surgical procedural element or the another element may, in use, be visible through the one or more through apertures, for instance with the surgical procedural element and the another element in an engaged state.

The first end of the mount body may be provided with an opening to a bore in the mount body. The other of the surgical procedural element or the another element may enter the bore through the mouth, for instance during the transition from a detached state to an engaged state for the surgical procedural element and the another element.

The opening may be provided with an increased radial profile, for instance the end most part of the opening. The opening may be provided with a chamfered perimeter.

The second end of the mount body may provide a connection for the mount body to the surgical procedural element or the another element. The connection may be a bore that receives the end of the surgical procedural element or the another element.

The mount body may have a longitudinal axis that extends through the mounting body and into the surgical procedural element or the another element. The longitudinal axis may be provided aligned with the axis of the bore in the first end of the mount body. The longitudinal axis may be aligned with the axis of movement of the surgical procedural element and the another element relative to one another, for instance when transitioning from a detached state to an engaged state and/or from an engage state to a detached state.

The first end of the mount body may be the end limit of both the mount body and the surgical procedural element or the another element the mount body is provided on. The first end of the mount body may be the proximal end when on the surgical procedural element. The first end of the mount body may be the distal end when on the another element.

The second end of the mount body may be the junction of the mount body with the surgical procedural element or the another element the mount body is provided on. The second end of the mount body may be distal to the proximal end when on the surgical procedural element. The second end of the mount body may be proximal to the distal end when on the another element.

The first surface profile section may be provided closer to the first end of the mount body than the second surface profile section. A third surface profile section may be provided, for instance further from the first end of the mount body that the first surface profile section and/or the second surface profile section.

The first surface profile section may be present for a section extending from the first end of the mount body to a limit closer to the second end of the mount body. The first surface profile section may be present for a section extending from the limit of an increased radial profile transition section provided at the opening at the first end of the mount body. Thus, the first surface profile section may be present for a section extending from adjacent to the first end of the mount body to a limit closer to the second end of the mount body.

The first surface profile section may have a consistent first radial profile. The first section profile may have a constant extent for the first radial profile. The consistent first radial profile may be a regular shape. The constant extent for the first radial profile may be a circle, such as when a circular cross-section is provided for the bore in the mount body.

The first surface profile section may have a consistent first radial profile and/or a constant extent for the whole of the section extending from one axial limit of the first surface profile section to the other axial limit of the first surface profile section. For instance, the first section profile may be that of a cylinder, such as a right cylinder.

The first surface profile section may extend from one limit to another limit closer to the second end of the mount body. The another limit may be the location where a first transition surface is provided. The first transition surface may be provided between the first surface profile section and the second surface profile section.

A first transition surface may provide for a change in radial profile from the first radial profile at least partially towards the second radial profile. The first transition surface may provide for a change in radial profile from the first radial profile to the second radial profile for at least one part of the second surface profile section. The transition to the second radial profile may continue within the second surface profile section for one or more other parts.

Where the first surface profile section is an internal surface, a first embodiment, the first transition surface may provide for an inward increase in at least a part of the radial profile of the first transition surface when compared with the first radial profile.

Where the first surface profile section is an external surface, a further embodiment, the first transition surface may provide for an outward increase in at least a part of the radial profile of the first transition surface when compared with the first radial profile.

The second surface profile section may be positioned intermediate the first profile section and a third surface profile section. The third surface profile section may provide for the connection of the mount body to the surgical procedural element or the another element.

The second radial profile may be partially defined by alignment elements provided at locations around the second surface profile section. The alignment elements may be provided in a regular pattern around the second profile. The alignment elements may be provided in the same plane, for instance perpendicular to the longitudinal axis.

Two or more or all alignment elements may be regularly spaced around the second surface profile section and/or regularly spaced to provide the second radial profile.

An intermediate area may be provided between two alignment elements within the second surface profile section. The intermediate area may be an area where the second radial profile is different to the second radial profile where an alignment element is present. An intermediate area may be provided between each adjacent alignment elements within the second surface profile section. The second surface profile section may include alternating alignment element then intermediate area sequences around the perimeter of the second surface profile section.

Two or more intermediate areas may be regularly spaced around the second surface profile section and/or regularly spaced to provide the second radial profile.

Where the second surface profile section is an internal surface, a first embodiment, one or more or all, of the alignment elements may provide for an inward increase in at least a part of the radial profile of the second radial profile when compared with the first radial profile. For instance, one or more or all, of the alignment elements may extend medially into the bore of the mount body.

Where the second surface profile section is an external surface, a further embodiment, one or more or all, of the alignment elements may provide for an outward increase in at least a part of the radial profile of the second radial profile when compared with the first radial profile. For instance, one or more or all, of the alignment elements may extend radially from the mount body.

One or more or all, of the intermediate areas may have the same radial profile as each other, for instance in one or more given planes perpendicular to the longitudinal axis. One or more or all, of the intermediate areas may have the same radial profile as each other in all planes. One or more or all, of the intermediate areas may have the same radial profile as each other in all axial planes or positions. One or more or all, of the intermediate areas may have a constant cross-sectional profile, for instance in planes perpendicular to the longitudinal axis.

One or more or all, of the alignment elements may have the same radial profile as each other, for instance in one or more given planes perpendicular to the longitudinal axis. One or more or all, of the alignment elements may have the same radial profile as each other in all planes. One or more or all, of the alignment elements may have a different radial profile at two or more different axial positions.

One or more or all, of the alignment elements may have a non-constant cross-sectional profile considered along a first part of the longitudinal axis. The first part of the longitudinal axis with the non-constant cross-section may be closer to the first surface profile section than a second part of the longitudinal axis where the cross-section is considered.

The non-constant cross-section along a first part of the longitudinal axis may define an alignment element transition part of the second surface profile section. The alignment element transition part may provide one or more abutment surfaces for one or more alignment elements. One or more or all, of the alignment element transition parts may include a first abutment surface inclined in one direction and a second abutment surface inclined in a second direction.

An incline transition surface, such as an apex surface, may be provided between a first abutment surface inclined in one direction and a second abutment surface inclined in a second direction. The apex surface may be curved. The apex surface may include an inflexion apex line defined by a series of points of inflexion between a first direction of inclination and a second direction of inclination.

The first direction of inclination and/or the second direction of inclination may include a component of the incline which is towards the second end of the mount and/or a component axially along the mount body. The first direction of inclination may include a component of the incline in one direction about the axis and/or about the mount body which has an opposite component to the incline in the second direction. The first abutment surface may be inclined in a first direction which is anticlockwise about a central axis and/or the second abutment surface may be inclined in a second direction which is clockwise about a central axis.

The first abutment surface may be provided with a further inclination direction, for instance inwards relative to the bore and/or towards a central axis. The further inclination direction may be an inward slope. The second abutment surface may be provided with a second further inclination direction, for instance inwards relative to the bore and/or towards a central axis. The second further inclination direction may be an inward slope. The further inclination direction and the second further inclination direction may be the same.

A first alignment element transition part, such as a first abutment surface, may be angled relative to a second alignment element transition part, such as a second abutment surface by an angle. The angle, for instance the internal angle between them, may be 150°+/−30°, for instance 150°+/−20°, such as 150°+/−15°. The angle may be defined between the first alignment element transition part, for instance a medial edge thereof, and the second alignment element transition part, for instance a medial edge thereof. The angle may be defined as the internal apex angle of an intersection of a first alignment element transition part, such as a first abutment surface, and a second alignment element transition part, such as a second abutment surface. The intersection can be of projections of a part of the first alignment element transition part, such as a part of the first abutment surface the planar surface, and a part of the second alignment element transition part, such as a part of the second abutment surface.

One or more or all of the alignment element transition parts, such as one or more or all of the abutment surface, may be angled relative to a longitudinal axis by an angle. The angle, for instance the internal angle between them, may be 45°+/−15°, for instance 45°+/−10°, such as 45°+/−5°. The angle may be defined between the longitudinal axis and a line extending across an alignment element transition part, such as an abutment surface. The line may extend across an alignment element transition part from a location on the distal side to the proximal side, potentially in the direction giving the shortest between the location and the proximal side. The angle may be defined between the longitudinal axis and a line extending across an alignment element transition part across the apex surface, such as along a line of inflection of the apex surface.

One or more of the alignment element transition parts, for instances one or more or all of the inclined transition surfaces, may be angled relative to a plane perpendicular to the longitudinal axis by an alternative angle. The alternative angle may be 15°+/−10°, for instance 15°+/−7°, such as 15°+/−5°.

One or more or all, of the alignment elements may have a constant cross-sectional profile considered along a second part of the longitudinal axis. The second part of the longitudinal axis with the constant cross-section may be further from the first surface profile section than a first part of the longitudinal axis where the cross-section is considered and, for instance varies.

The constant cross-section along a second part of the longitudinal axis may define two or more planar surfaces, for instance, which in use, transmit torque. The constant cross-section along a second part may provide a cross-section formed of a regular set of planar parts, for instance a hexagonal cross-section. The cross-section of the planar part of the second surface profile section may be different from a circular cross-section part of the first surface profile section.

The alignment element transition parts may be provided axially before the constant cross-sectional profile, when transitioning from a detached state to an engaged state.

The mounting component may have a detached state in which the surgical procedural element is not connected with the another element. The mounting component may have an engaged state in which the surgical procedural element is connected to the another element.

The mounting component may have a transition state. The transition state may be intermediate the detached state and the engaged state.

The mounting component, for instance the mount body, may be separate from a second mounting component in the detached state. The mounting component, for instance the mount body, may be in contact with a second mounting component in the transition state. The mounting component, for instance the mount body, may be in contact with the second mounting component in the engaged state. Particularly, the planar surfaces of the second surface profile section may be opposed and/or in contact with the second mounting component, particularly one or more planar surfaces of the second mounting component.

The longitudinal axis separation of the mounting component and the second mounting component may be greater than in the transition state and/or engaged state.

The length of the surgical procedural element within the another element or the length of the another element within the surgical procedural element may be less in the transition state than in the engaged state. The length of the surgical procedural element within the another element or the length of the another element within the surgical procedural element may be at a maximum in the engaged state.

The rotational positions possible, for instance about the longitudinal axis, for the surgical procedural element relative to the another element or for the another element relative to the surgical procedural element may be unconstrained in the detached state.

The rotational position possible, for instance about the longitudinal axis, for the surgical procedural element relative to the another element or for the another element relative to the surgical procedural element may be constrained in the engaged state. A plurality of distinct rotational positions for the surgical procedural element relative to the another element or for the another element relative to the surgical procedural element may be possible in the engaged state. The distinct rotational positions may be separate from intermediate rotational positions that are not possible. In a distinct rotational position, movement of the surgical procedural element relative to the another element or movement of the another element relative to the surgical procedural element may be constrained to less than $1^{0}$, for instance to a fitting tolerance.

The rotational positions possible, for instance about the longitudinal axis, for the surgical procedural element relative to the another element or for the another element relative to the surgical procedural element may be unconstrained in a first part of the transition state. The rotational positions possible, for instance about the longitudinal axis, for the surgical procedural element relative to the another element or for the another element relative to the surgical procedural element may be partially constrained in a second part of the transition state. The rotational positions possible, for instance about the longitudinal axis, for the surgical procedural element relative to the another element or for the another element relative to the surgical procedural element may be constrained in a third part of the transition state.

In the transition state, particularly in a first part of the transition state, axial movement of the surgical procedural element and the another element relative to one another may be provided without causing relative rotational movement of the surgical procedural element and the another element relative to one another.

In the transition state, particularly in a second part of the transition state, axial movement of the surgical procedural element and the another element relative to one another may be provided which causes relative rotational movement of the surgical procedural element and the another element relative to one another. An axial force applied to one of the surgical procedural element and the another element may cause the rotation.

In the transition state, particularly in a third part of the transition state, axial movement of the surgical procedural element and the another element relative to one another may be provided without causing relative rotational movement of the surgical procedural element and the another element relative to one another. An axial force applied to one of the surgical procedural element and the another element may cause axial movement only.

The transition state may include a first part of the state and/or a second part of that state and/or a third part of that state. The mounting component may move from a detached state to a first part of the transition state and then subsequently to an engaged state. The mounting component may move from a detached state to a first part of the transition state, then subsequently a second part of the transition state and then subsequently to an engaged state. The mounting component may move from a detached state to a first part of the transition state, then subsequently a second part of the transition state, then subsequently to a third part of the transition state and then subsequently to an engaged state. The sequence may be reversed in moving from an engaged state to a detached state.

The first aspect of the disclosure may include any of the other feature features, options or possibilities set out herein, including in the other aspects of the disclosure, and including when any are taken singularly or in any combination.

According to a second aspect of the disclosure there is provided a second mount component, which may be adapted to cooperate with the mount component of the first aspect, the second mount component comprising:

a second mount body provided at an end of the another element or at the end of the surgical procedural element; wherein:

the second mount body has a first end and a second end, the second mount body has a longitudinal axis, the first end being spaced from the second end along the longitudinal axis, the second mount body has a first surface profile section, the first surface profile section including a first radial profile considered perpendicular to the longitudinal axis;

the second mount body has a second surface profile section, the second surface profile section being closer to the second end of the second mount body than the first surface profile section, the second surface profile section including a second radial profile considered perpendicular to the longitudinal axis and parallel to the first radial profile;

wherein the second surface profile section is at least partially defined by one or more alignment elements and the second radial profile has a different radial profile to the first radial profile surface due to the presence of the one or more alignment elements.

The second mounting component may have any of the features, options and possibilities set out in the first aspect of the disclosure in relation to the mounting component.

The second mounting component may be connected to a surgical procedural element or to a further element, or may be an integral part thereof.

The second mounting component may be a male component, in a first embodiment, with the mounting component a female component. The female component may be provided on the another element.

The second mounting component may be a female component, in a further embodiment, with the mounting component a male component. The male component may be provided on the surgical procedural element.

Where the second mounting component is a male component, a first embodiment, the second surface profile section may have a different radial profile to the first radial profile surface due to the presence of the one or more alignment elements and the one or more alignment elements increasing the second radial profile in those parts of the second radial profile for which they are present. The one or more alignment elements may extend radially outward. The one or more alignment elements may extend radially outward away from an external surface of the second mount body.

Where the second mounting component is a female component, a further embodiment, the second surface profile section may have a different radial profile to the first radial profile surface due to the presence of the one or more alignment elements and the one or more alignment elements reducing the second radial profile in those parts of the second radial profile for which they are present. The one or more alignment elements may extend radially inward. The one or more alignment elements may extend radially inward into a bore in the second mount body.

The second mount body may include an external wall. The external wall may at least partially enclose an internal bore. The external wall may define an external surface profile section for the second mount body. The external surface profile section may be at least partially cylindrical. The external surface profile section may include two or more partially cylindrical profile parts, for instance with intermediate profile parts between them. The external surface profile section may include two or more planar profile parts. One or more or all, of the intermediate profile parts may be provided by planar profile parts. The external surface profile section may be defined in part by alternating planar profile parts and partially cylindrical profile parts. One or more or all of the planar parts may have a reduced radial extent compared with the radial extent of one or more or all of the partially cylindrical profile parts.

One or more external profile parts, for instance one or more or all, of the planar profile parts, may, in use, provide for the application of torque to the second mount body.

The first end of the second mount body may be provided with an opening to a bore in the mount body.

The first end of the second mount body may enter the bore of a mount body, for instance during the transition from a detached state to an engaged state for the surgical procedural element and the another element.

The first end of the second mount body may have an annular profile. The first end of the second mount body may include an annular surface generally perpendicular to the longitudinal axis.

The second mount body may have a longitudinal axis that extends through the second mount body and into the surgical procedural element or the another element. The longitudinal axis may be the same as the longitudinal axis of the mounting component of the first aspect, for instance in use, such as in the transition state and/or engaged state.

The first surface profile section for the second mounting component may have a consistent first radial profile. The first section profile may have a constant extent for the first radial profile. The consistent first radial profile may be a regular shape. The constant extent for the first radial profile may be a circle, such as when a circular cross-section is provided for the bore in the mount body.

The first section profile of the second mounting component may be relatively short, for instance less than a third the length of the second section profile of the second mounting component.

On the second mounting component, a first transition surface may provide for a change in radial profile from the first radial profile at least partially towards the second radial profile. The first transition surface may provide for an outward increase in at least a part of the radial profile of the first transition surface when compared with the first radial profile.

The second radial profile of the second mounting component may be partially defined by alignment elements provided at locations around the second surface profile section. The second radial profile of the alignment elements of the second mounting component may correspond in profile to the second radial profile of the intermediate elements of the mounting component.

The second radial profile of the second mounting component may be partially defined by intermediate elements provided at locations around the second surface profile section. The second radial profile of the intermediate elements of the second mounting component may correspond in profile to the second radial profile of the alignment elements of the mounting component.

One or more or all, of the alignment elements may provide for an increase of at least a part of the radial profile of the second radial profile when compared with the first radial profile. For instance, one or more or all, of the alignment elements may extend radially outward from the mount body.

One or more or all, of the intermediate elements may provide for an decrease in at least a part of the radial profile of the second radial profile when compared with the second radial profile of the one or more alignment elements. For instance, one or more or all, of the intermediate elements may be planar surfaces with an outward radial extent less than the one or more alignment elements.

One or more or all, of the alignment elements may have the same radial profile as each other, for instance in one or more given planes perpendicular to the longitudinal axis. One or more or all, of the alignment elements may have the same radial profile as each other in all planes. One or more or all, of the alignment elements areas may have the same radial profile as each other in all axial planes or positions. One or more or all, of the alignment elements may have a constant cross-sectional profile, for instance in planes perpendicular to the longitudinal axis.

One or more or all, of the intermediate areas may have the same radial profile as each other, for instance in one or more given planes perpendicular to the longitudinal axis. One or more or all, of the intermediate areas may have the same radial profile as each other in all planes. One or more or all, of the intermediate areas may have a different radial profile at two or more different axial positions.

One or more or all, of the intermediate areas may have a non-constant cross-sectional profile considered along a first part of the longitudinal axis. The first part of the longitudinal axis with the non-constant cross-section may be further from the first surface profile section than a second part of the longitudinal axis where the cross-section is considered.

The second aspect of the disclosure may include any of the other feature features, options or possibilities set out herein, including in the other aspects of the disclosure, and including when any are taken singularly or in any combination.

According to a third aspect of the disclosure there is provided a kit, the kit comprising:

a) one or more surgical procedural elements;

b) one or more another elements;

wherein at least one of the surgical procedural elements or at least one of the further elements is provided with a mounting component according to the first aspect of the disclosure or with a second mounting component according to the second aspect of the disclosure.

The kit may include a plurality of surgical procedural elements each provided with the same mounting component as each other. The kit may include a plurality of another elements each provided with the same mounting component as each other.

The one or more or all, another elements may be provided with a mounting component according to the first aspect.

The one or more or all, surgical procedural elements may be provided with a second mounting component according to the second aspect.

The third aspect of the disclosure may include any of the other feature features, options or possibilities set out herein, including in the other aspects of the disclosure, and including when any are taken singularly or in any combination.

According to a fourth aspect of the disclosure there is provide a method of attaching a surgical procedural element to a another element:

wherein at least one of the surgical procedural element or another element are provided with a mounting component according to the first aspect of the disclosure or a second mounting component according to the second aspect of the disclosure on an end;

the method comprising the steps of:

inserting an end of one of a surgical procedural element or another element into the other;

advancing one of the surgical procedural element and another element into the other axially until one or more alignment elements of the provided mounting component abut a location on the other of the surgical procedural element or the another element;

providing axial force to one or both of the surgical procedural element and the another element, the one or more alignment elements providing a rotational component to the surgical procedural element and the another element as a part of further advance of one of the surgical procedural element and the another element into the other axially.

The method may include the mounting component having a detached state in which the surgical procedural element is not connected with the another element. The mounting component may have an engaged state in which the surgical procedural element is connected to the another element.

The mounting component may have a transition state. The transition state may be intermediate the detached state and the engaged state.

The mounting component, for instance the mount body, may be separate from a second mounting component in the detached state. The mounting component, for instance the mount body, may be in contact with a second mounting component in the transition state. The mounting component, for instance the mount body, may be in contact with the second mounting component in the engaged state. Particularly, the planar surfaces of the second surface profile section may be opposed and/or in contact with the second mounting component, particularly one or more planar surfaces of the second mounting component.

The longitudinal axis separation of the mounting component and the second mounting component may be greater in the disengaged state than in the transition state and/or engaged state.

The length of the surgical procedural element within the another element or the length of the another element within the surgical procedural element may be less in the transition state than in the engaged state. The length of the surgical procedural element within the another element or the length of the another element within the surgical procedural element may be at a maximum in the engaged state.

The rotational positions possible, for instance about the longitudinal axis, for the surgical procedural element relative to the another element or for the another element relative to the surgical procedural element may be unconstrained in the detached state.

The rotational position possible, for instance about the longitudinal axis, for the surgical procedural element relative to the another element or for the another element relative to the surgical procedural element may be constrained in the engaged state. A plurality of distinct rotational positions for the surgical procedural element relative to the another element or for the another element relative to the surgical procedural element may be possible in the engaged state. The distinct rotational positions may be different from intermediate rotational positions that are not possible. In a distinct rotational position, movement of the surgical procedural element relative to the another element or movement of the another element relative to the surgical procedural element may be constrained to less than $1^{0}$, for instance to a fitting tolerance.

The rotational positions possible, for instance about the longitudinal axis, for the surgical procedural element relative to the another element or for the another element relative to the surgical procedural element may be unconstrained in a first part of the transition state. The rotational positions possible, for instance about the longitudinal axis, for the surgical procedural element relative to the another element or for the another element relative to the surgical procedural element may be partially constrained in a second part of the transition state. The rotational positions possible, for instance about the longitudinal axis, for the surgical procedural element relative to the another element or for the another element relative to the surgical procedural element may be constrained in a third part of the transition state.

In the transition state, particularly in a first part of the transition state, axial movement of the surgical procedural element and the another element relative to one another may be provided without causing relative rotational movement of the surgical procedural element and the another element relative to one another.

In the transition state, particularly in a second part of the transition state, axial movement of the surgical procedural element and the another element relative to one another may be provided which causes relative rotational movement of the surgical procedural element and the another element relative to one another. An axial force applied to one of the surgical procedural element and the another element may cause the rotation.

In the transition state, particularly in a third part of the transition state, axial movement of the surgical procedural element and the another element relative to one another may be provided without causing, relative rotational movement of the surgical procedural element and the another element relative to one another. An axial force applied to one of the surgical procedural element and the another element may cause axial movement only.

The transition state may include a first part of the state and/or a second part of that state and/or a third part of that state. The mounting component may move from a detached state to a first part of the transition state and then subsequently to an engaged state. The mounting component may move from a detached state to a first part of the transition state, then subsequently a second part of the transition state and then subsequently to an engaged state. The mounting component may move from a detached state to a first part of the transition state, then subsequently a second part of the transition state, then subsequently to a third part of the transition state and then subsequently to an engaged state. The sequence may be reversed in moving from an engaged state to a detached state.

The first part of the transition state may end when there is abutment between one or more alignment elements and a location on the other of the surgical procedural element or a location on the another element. The location may be an intermediate area of the other of the surgical procedural element or the another element.

The second part of the transition state may start when there is abutment between one or more alignment elements and a location of the other of the surgical procedural element or a location of the another element. The second part of the transition state may include a rotational component to the surgical procedural element and the another element movement. The second part of the transition state may include axial movement of the surgical procedural element and the another element movement. The second part of the transition state may include axial movement of the surgical procedural element and the another element movement which is conditional on a rotational component to the movement of the surgical procedural element and the another element. The second part of the transition state may end when there is no further rotational component to the surgical procedural element and the another element movement. The second part of the transition state may end when further rotational movement of the surgical procedural element and the another element is constrained.

The second part of the transition state may include movement of a location of the other of the surgical procedural element or a location of the another element along a surface of one or more alignment elements, for instance an inclined surface thereof.

The third part of the transition state may start when there is no further rotational component to the surgical procedural element and the another element movement. The third part of the transition state may start when further rotational movement of the surgical procedural element and the another element is constrained. The third part of the transition state may include further axial movement of the surgical procedural element and the another element relative to one another. The further axial movement may be possible because of the alignment of the location of the other of the surgical procedural element or the location of the another element with a gap through the alignment elements. The further axial movement may be possible because of the alignment of the location of the other of the surgical procedural element or the location of the another element with an intermediate area between the alignment elements. The third part of the transition state may end when no further axial movement of the surgical procedural element and the another element is possible.

The engaged state may be provided when no further axial movement of the surgical procedural element and the another element is possible. The engaged state may be provided when rotational movement of one of the surgical procedural element and the another element causes rotational movement of the other.

The engaged state may provide for torque transfer from the another element to the surgical procedural element. The engaged state may provide one or more planar surfaces of the another element in opposition to one or more planar surfaces of the surgical procedural element. For instance, six planar surfaces may be in opposition with six planar surfaces.

The fourth aspect of the disclosure may include any of the other feature features, options or possibilities set out herein, including in the other aspects of the disclosure, and including when any are taken singularly or in any combination.

BRIEF DESCRIPTION OF THE DRAWINGS

Various embodiments of the disclosure will now be described, by way of example only, and with reference to the accompanying drawings in which.

DETAILED DESCRIPTION OF THE DRAWINGS

Figure 1A:
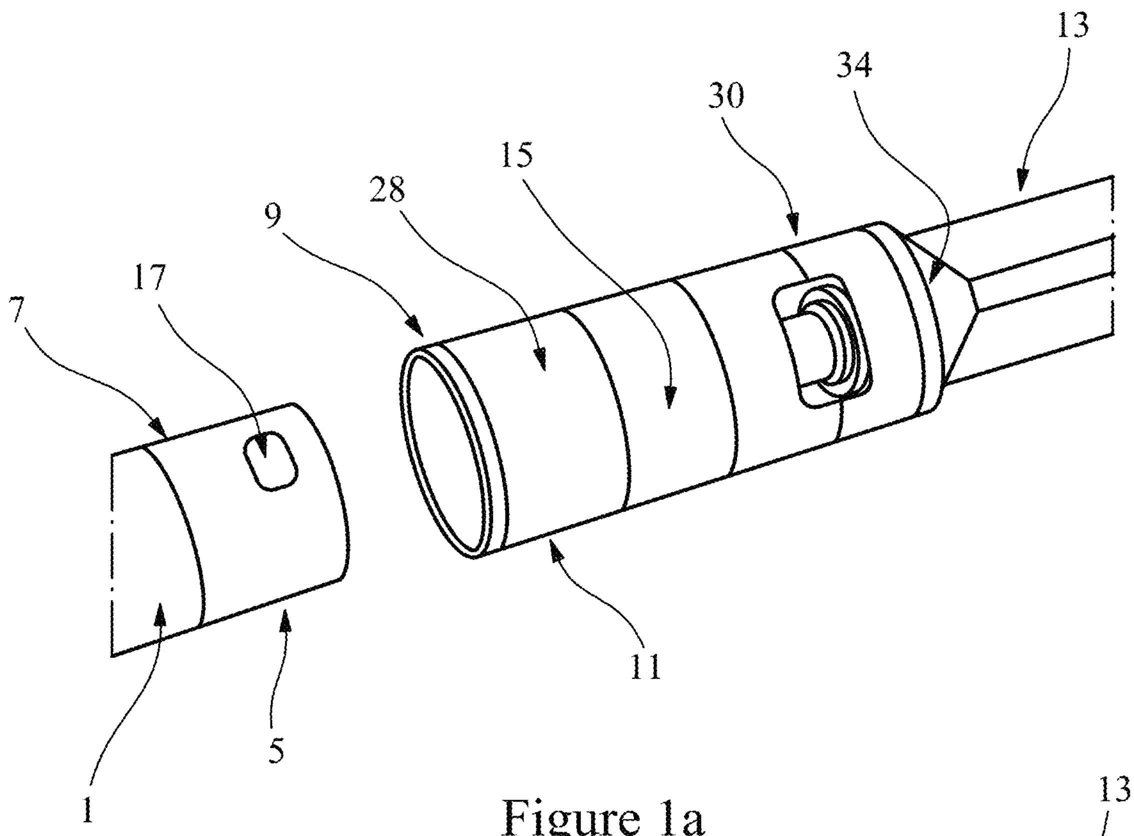
FIGS. 1*a* and 1*b* show a prior art distal reamer to distal reamer extension connection approach.

In a variety of situations, there is a need to provide a mounting system for a surgical procedural element. A particular instance where such mounting systems find use is in hip replacement procedures.

- The surgical procedural element can be a surgical instrument. Reamers, broaches and rasps are all examples of such surgical instruments and hence surgical procedural elements. They find particular application in the preparation of the femur to receive a femoral component of a hip replacement. During the procedure it is necessary to prepare the femoral canal so that it is hollowed out, in the appropriate shape, to receive the stem of the femoral component.
- The surgical procedural element can be a trial component. For instance, trial stems are used to check the intended position being set up for the femoral component of a hip replacement and so are examples of such surgical procedural elements.
- The surgical procedural element may be a final component left in-situ after the surgical procedure, for instance the stem of the hip replacement.

In general, the surgical procedural element 1 is provided with a distal end where, in the case of a reamer the cutting blades 3 are provided, and a proximal end 5 where a first connection element 7 is provided. The first connection element 7 cooperates with a second connection element 9 provided on the distal end 11 of a force applicator or extension element 13.

In operation, a first surgical procedural element 1 is attached to the force applicator 13, is used and then needs to be swapped for a second surgical procedural element 13 and potentially further surgical procedural elements 13. Thus a series of connecting and disconnecting actions need to be performed. FIG. 1*a* illustrates a disconnected and FIG. 1*b* a connected state for the two elements.

As an example, a set of reamers 1 is often provided with sequential increases in diameter so that the reamers 1 can be used in turn to hollow out the femur to the desired diameter.

Figure 1B:
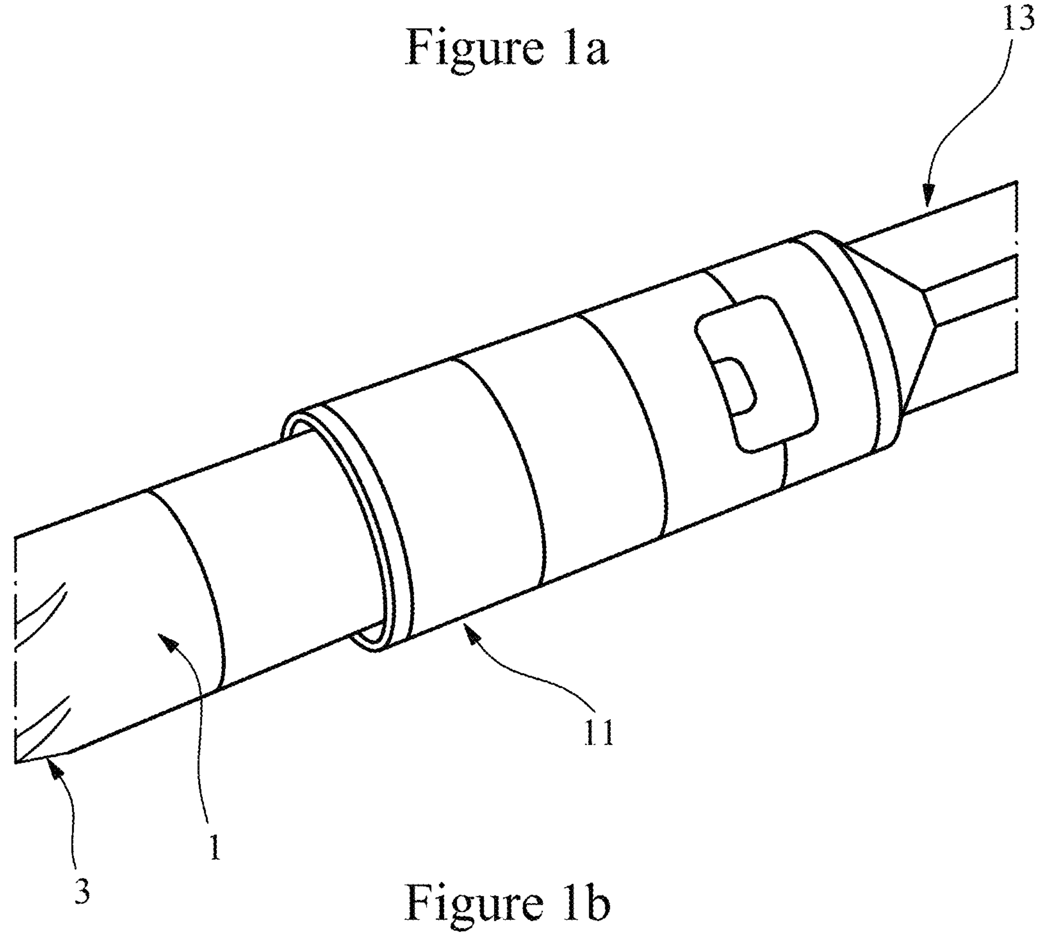

To connect the distal end 11 of the force applicator 13 or extension element 13 to the proximal end 5 of the surgical procedural element 1, an arrangement as shown in FIGS. 1*a* and 1*b* can be employed. The proximal end 5 of the surgical procedural element 1 has an external diameter less than the internal diameter of a collar 15 on the distal end 11 of the extension element 13. This allows the proximal end 5 to slide inside the extension element 11. A spigot and socket type arrangement is thus provided. An engagement is provided, after insertion by rotating the surgical procedural element 1 and the extension element 13 relative to one another to cause an interaction between the L-shaped slot 17 on the proximal end 5 and an internal element [not shown] within the collar 15.

To overcome the inherent resistance due to contact between the surgical procedural element 1 and the extension element 13, an active twist action needs to be applied to one or both of the surgical procedural element 1 and/or extension element 13. This can be awkward to achieve, means that rotational load is applied before the actual engagement is present and may require verification to ensure proper alignment and engagement has been achieved. It is desirable to overcome these issues.

Whilst the context for the disclosure is described above in relation to a reamer 1 as the surgical procedural element 1, a wide variety of different surgical procedural elements 1 are suitable for adoption of the present disclosure. Thus, a variety of different shape reamers 1 can be used. Different reamer shapes are often used for the distal femoral canal preparation compared with those used in the proximal femoral canal preparation and/or intermediate femoral canal, for instance due to the different size and shape hollow required for different parts of the femoral component of the hip replacement that is to be inserted.

In other situations or procedures, it may be preferred to use one or more broaches in the preparation of the hollow, one or more rasps or combinations of reamers, broaches and rasps. These can be connected to the extension element 13 in an equivalent manner.

In addition to use in forming the hollow, the extension element 13 or force applicator 13 can be used to introduce a trial stem and/or a final stem.

Figure 2:
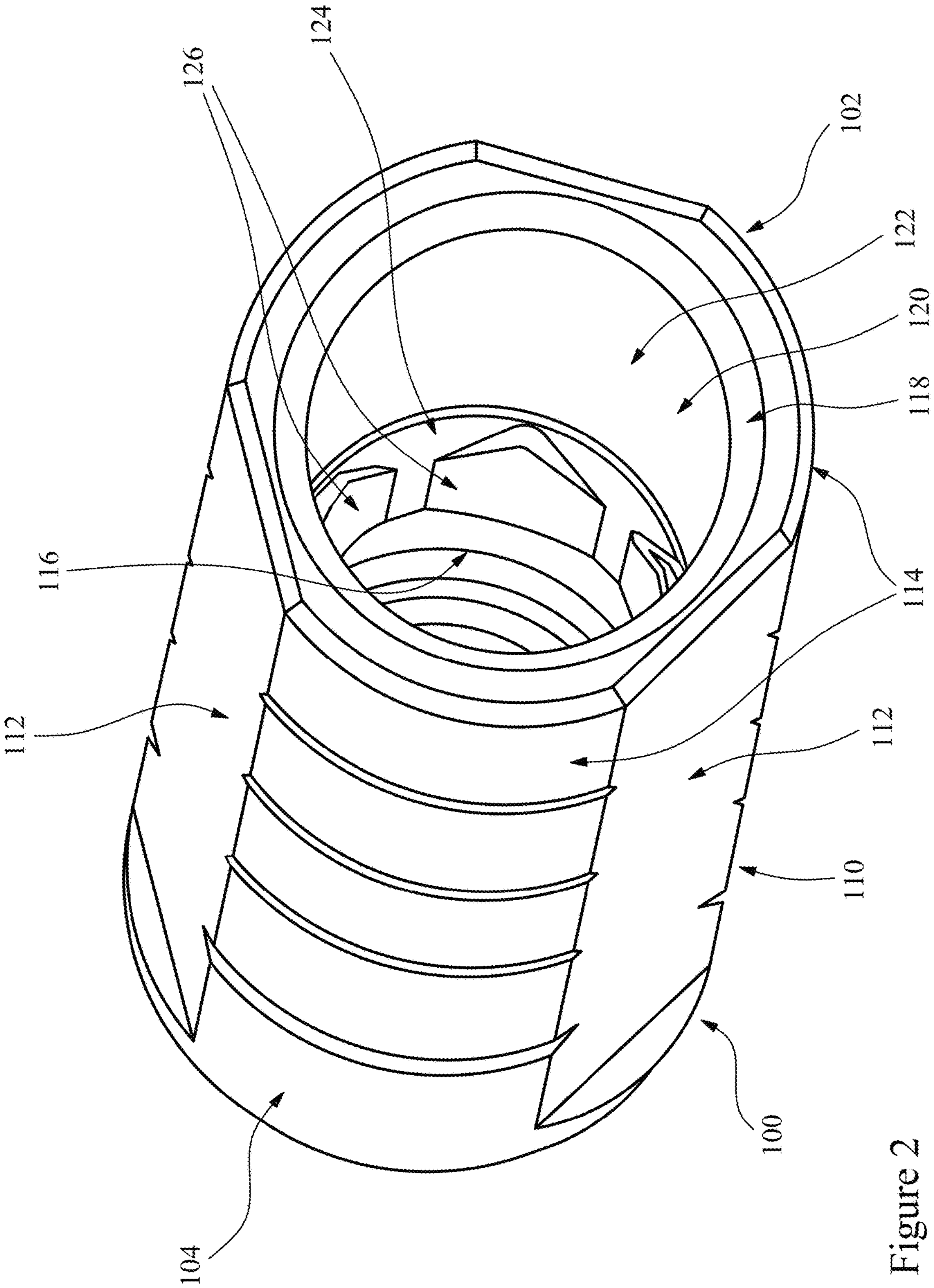
FIG. 2 shows a perspective view of the female component of a mounting system according to an embodiment of the disclosure.

Referring to FIG. 2, a perspective view of a female component 100 of the mounting system according to a first embodiment is seen. Consistent with the format seen in FIGS. 1*a* and 1*b*, the female component 100 is provided at the distal end 102 of the extension element [not shown], which would extend away from the proximal end 104 of the female component 100. The female component 100 would typically be welded onto the distal end of the extension element [not shown]. The extension element would include connection features to allow the application of torque and/or tension and/or compression to the extension element and hence to the female component 100, to the male component 106 and to the surgical procedural element 108. Thus, the male component 106 [see FIG. 8*a*, 8*b*, 8*c*] is provided on the surgical procedural element 108. Of course, the elements provided with the female component 100 and male component 106 could be reversed.

The external wall 110 of the female component 100 has three planar sections 112 and three part-cylindrical sections 114 intermediate those. Whilst loads will typically be applied to the extension element, the planar sections 112 allow interface with a tool [not shown] to allow torque to be applied at the female component 100 location, if needed.

The female component 100 surrounds a bore 116 which is provided with a mouth through which the male component 106 is received, the mouth being provided with a chamfered perimeter 118 to assist the location of the male component 106 into the bore 116.

The mouth end 120, the distal end 102 as described in this embodiment, of the female component 100 is provided with a first internal profile section 122 which is cylindrical in profile and smooth. The first internal profile section 122 leads to a second internal profile section 124 where aligners 126 are provided, as can be seen in more detail in FIG. 3.

The second internal profile section 124 is positioned intermediate the first profile section 122, through which the male component 106 is received, and a third profile section 128.

The third profile section 128 is provided with an appropriate configuration to receive and engage with the extension element [not shown] that the female component is mounted on the distal end 102 of.

Figure 3:
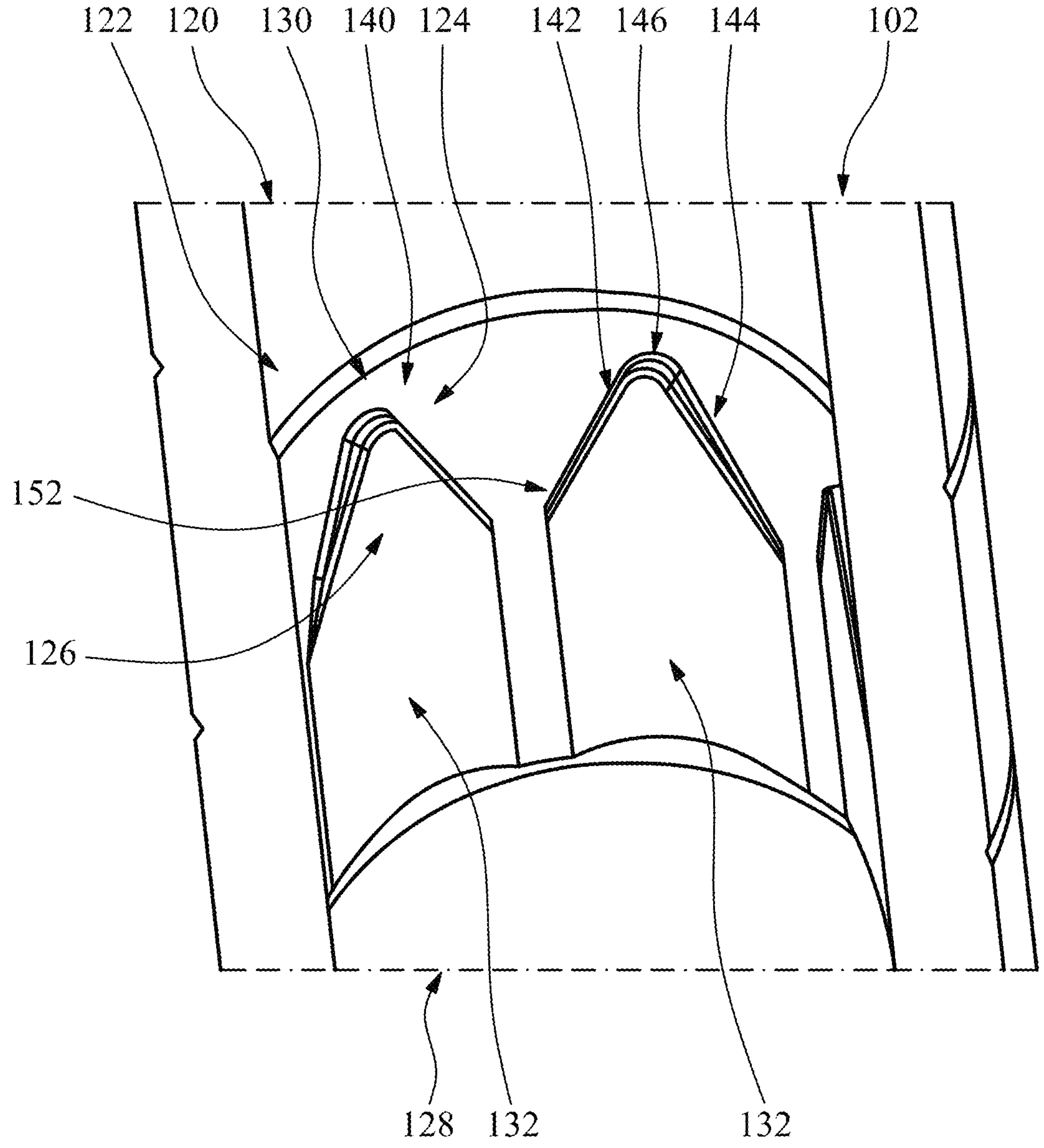
FIG. 3 shows a cross-sectional perspective view of details of the female component of FIG. 2.

Referring to FIG. 3, a transition surface 130 is provided at the boundary between the first profile section 122 and the second profile section 124 and represents a decrease in the cross-section of the bore 116. In this illustrated example, the decrease in cross-section is evenly provided and so represents a decrease in cross-sectional radius.

Figure 8A:
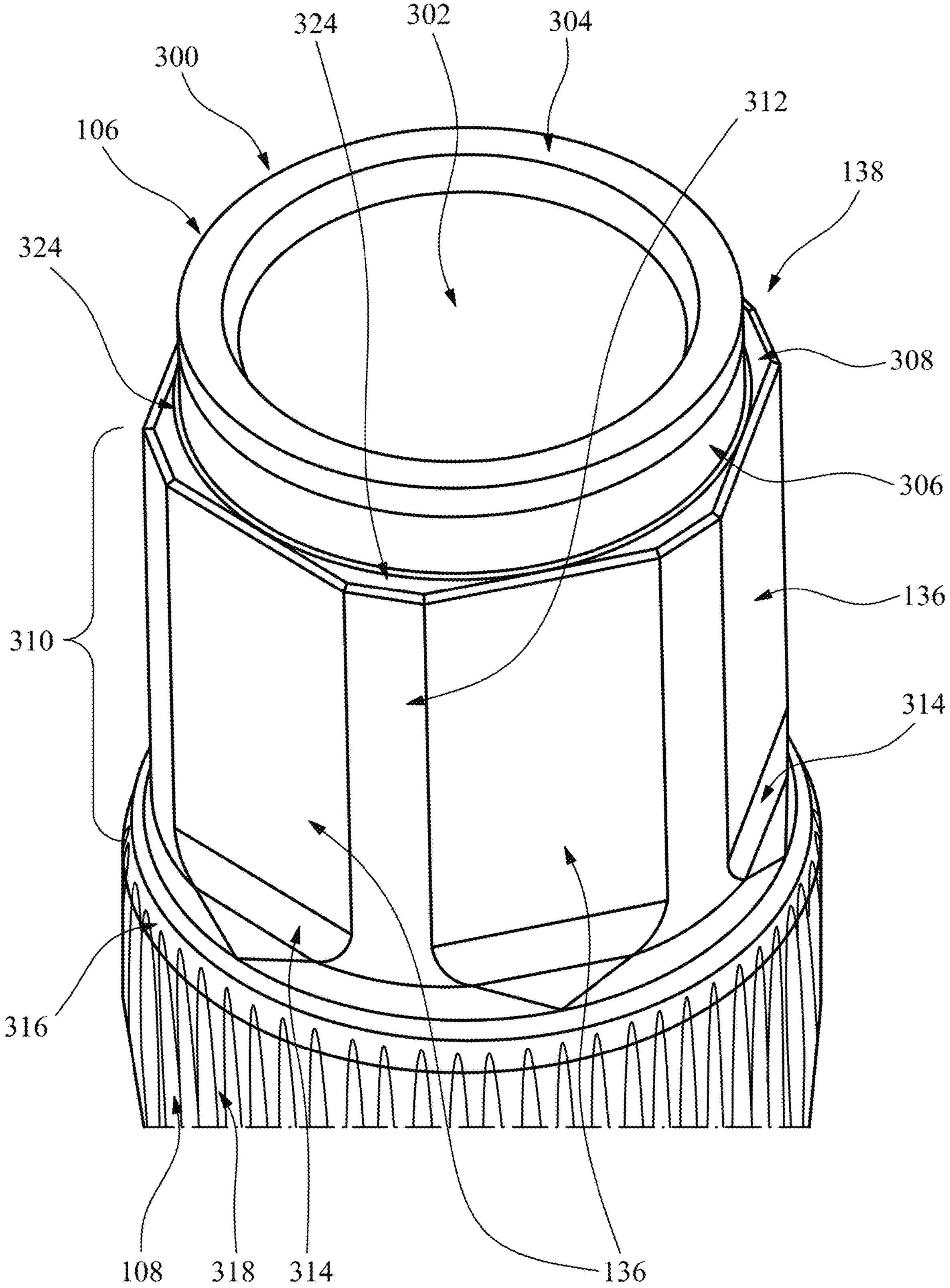
FIG. 8*a* shows a perspective view of a male component suitable for engagement with the female component of the FIGS. 2, 3 and 4 embodiment and particularly the FIGS. 5, 6 and 7 embodiment.
Figure 9:
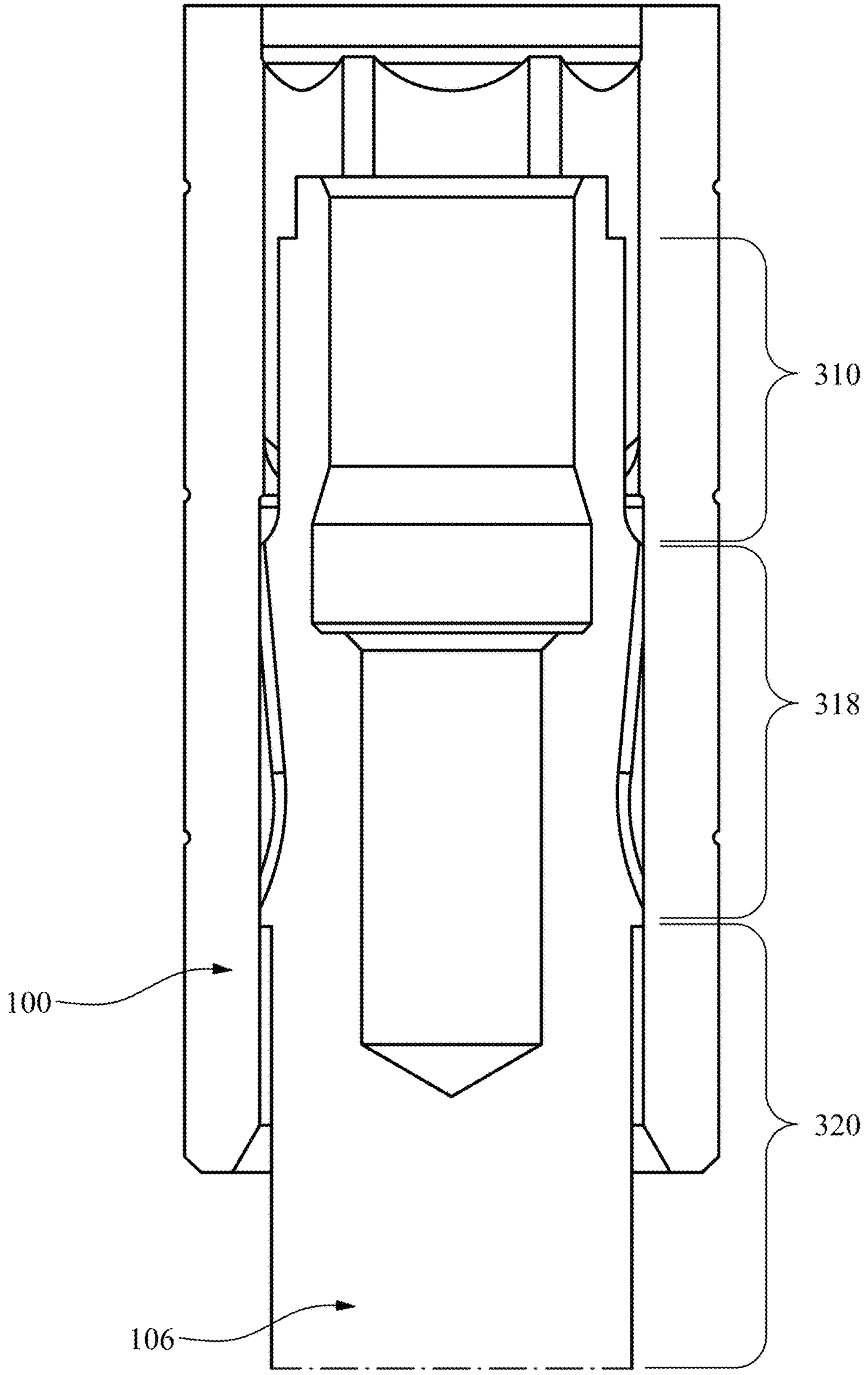
FIG. 9 is a cross-sectional side view of the female component of FIGS. 5, 6 and 7 engaged with a male component of FIGS. 8*a*, 8*b* and 8*c;*

In the second profile section 124 a series of planar surfaces 132 are provided around the internal perimeter of the bore 116. In the illustrated example six such planar surfaces are provided to provide a set of engagement surfaces 134, which in use, engage with corresponding engagement surfaces 136 on the outside surface 138 of the male component 106 [as shown in FIG. 8*a*]. The interaction of the set of female engagement surfaces 134 and male engagement surfaces 136, in use, allows the effective transmission of torque between the two components [as shown in FIG. 9].

Returning to FIG. 3, still within the second profile section 124, but closer to the mouth end 120 [the distal end 102 as shown] than the series of planar surfaces 132, the aligners 126 are provided.

Figure 4:
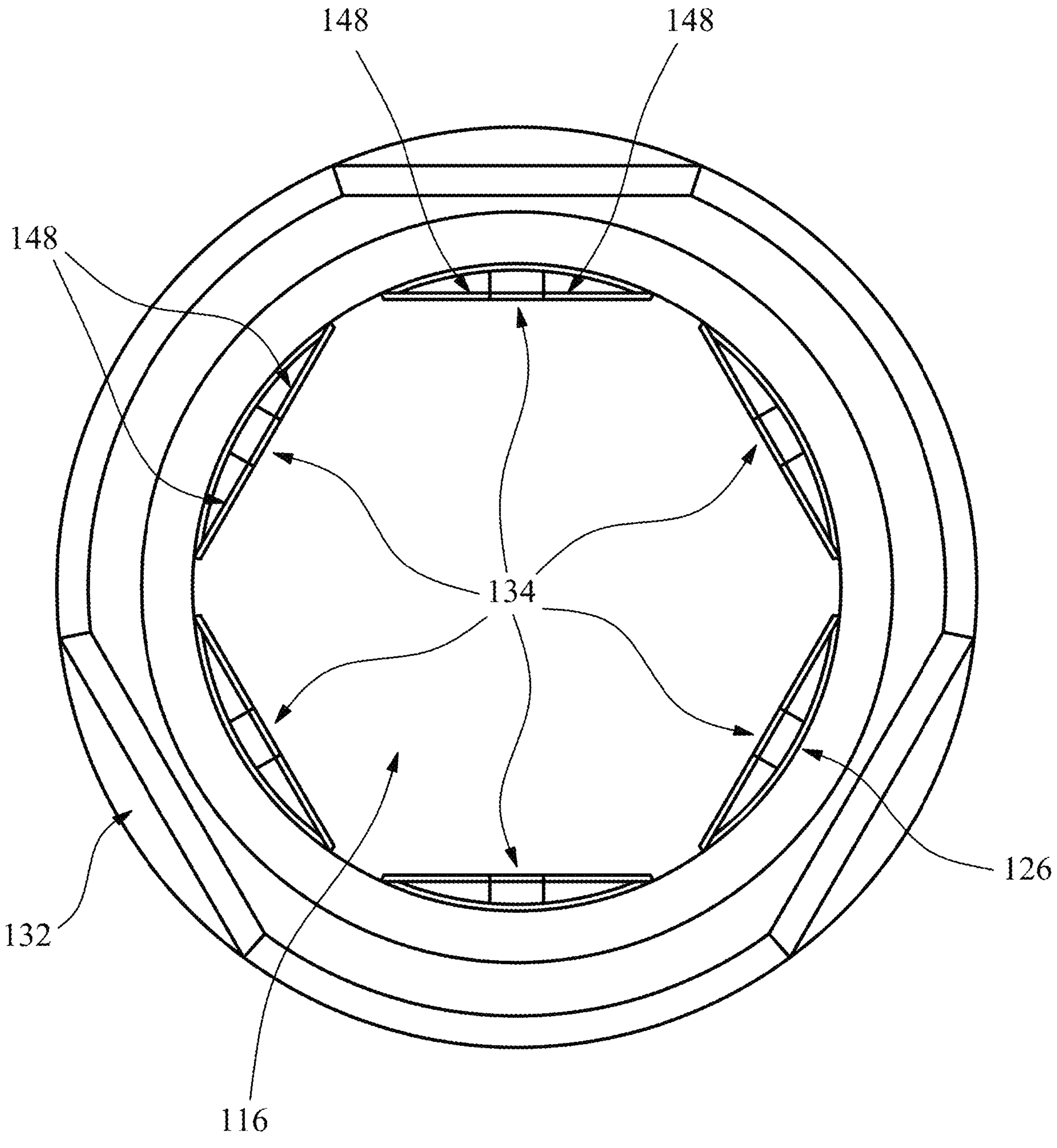
FIG. 4 shows a longitudinal axis view of the female component of FIGS. 2 and 3.

As can be seen in FIG. 4, each aligner 126 extends medially into the bore 116. The medial extent of each aligner 126 is configured such as to vary the cross-sectional profile from the circular cross-sectional profile seen at the start 140 of the second profile section 124 to the hexagonal cross-sectional profile seen at further locations 142 into the second profile section 124.

Whilst the male engagement surfaces 136 on the male component 106 can be presented at any rotation within the bore 116, whilst only extending into the first profile section 122 of the bore 116 or still whilst only extending into the start of the second profile section 124, alignment of the female engagement surfaces 134 and male engagement surfaces 136 must occur before those can be brought into engagement.

Rather than having to rotate actively the male component 106 and/or female component 100 relative to one another to find this engagement alignment, the disclosure uses the aligners 126 to achieve the alignment needed.

As can be seen in FIG. 3, each aligner 126 is positioned axially in front of a planar surface 132, considered relative to the insertion of the male component 106 into the female component 100. The aligner 126 defines a first alignment surface 142 and a second alignment surface 144 with an apex surface 146 provided between them. The apex surface 146 is curved to provide a smooth transition between the first alignment surface 144 and the second alignment surface 144.

The first alignment surface 142 has an extent axially within the bore 116 and also has an extent annularly around the bore 116 and so defines an inclined surface.

The second alignment surface 144 is similarly provided, but extends annularly in the opposite direction and so defines an opposite inclined surface.

The medial profile 148 of the aligners 126 corresponds to that of the planar surface 132 it leads to.

Full details of the corresponding design of the male component 106 are to be seen in FIGS. 8*a*, 8*b* and 8*c* and are described in detail below. Before that, a second embodiment of the female component is discussed, with reference to FIGS. 5, 6 and 7.

The second embodiment of the female component 100 has many features in common with the first embodiment and so this discussion there of focusses on the differences between the two. Like components in the two embodiments are given matching reference numerals in the drawings.

Figure 5:
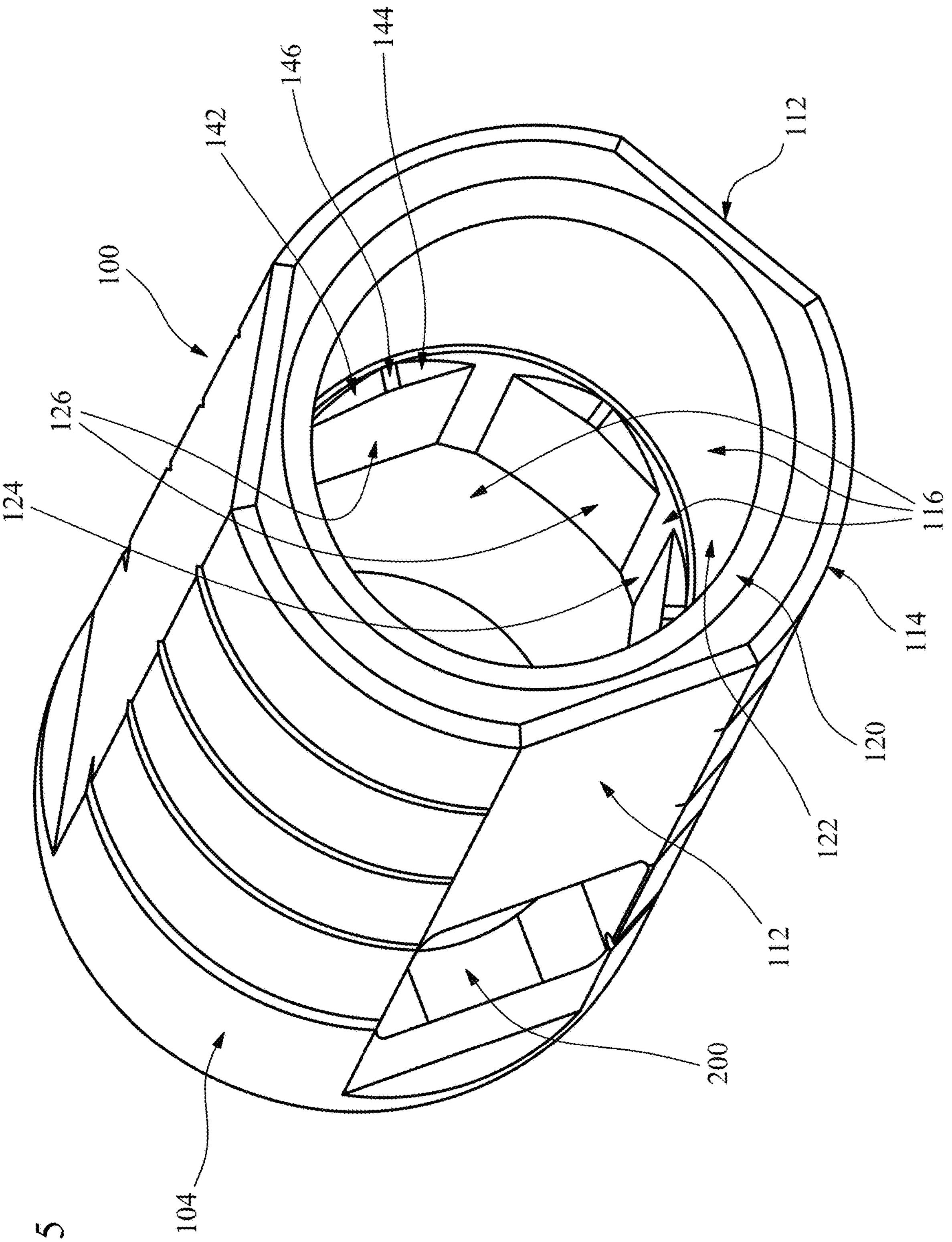
FIG. 5 shows a perspective view of the female component of a mounting system according to another embodiment of the disclosure.

Referring to FIG. 5, the perspective view of a female component 100 shows the proximal end 104 of the female component 100, the external wall 110 of the female component 100 and the three planar sections 112 and the three part-cylindrical sections 114 intermediate those. Whilst loads will typically be applied to the extension element, the planar sections 112 allow interface with a tool [not shown] to allow torque to be applied at the female component 100 location, if needed.

The female component 100 surrounds a bore 116 which receives the male component 106 in use. The mouth end 120 is provided with a first internal profile section 122 which leads to a second internal profile section 124 where the aligners 126 are provided, as before.

Figure 6:
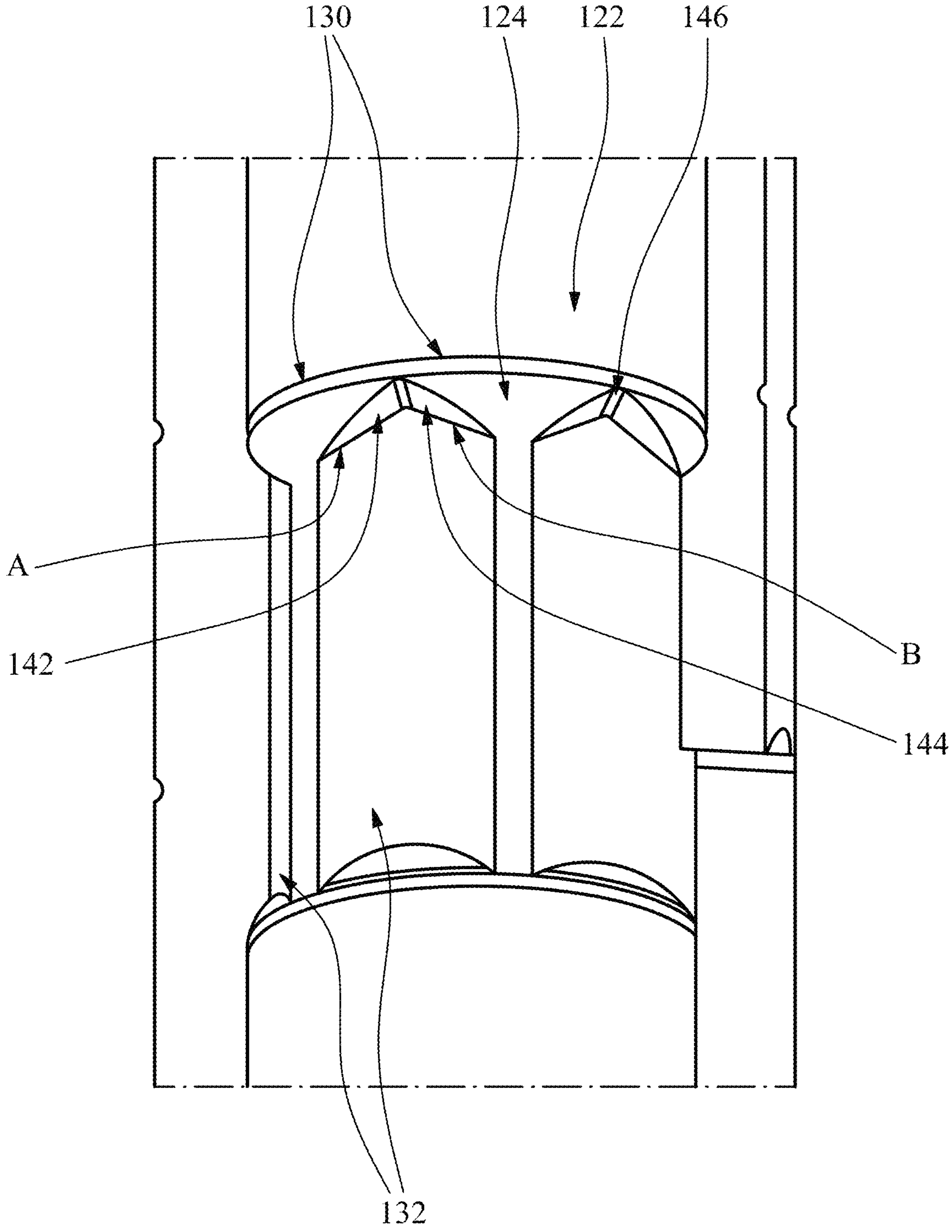
FIG. 6 shows a cross-sectional perspective view of details of the female component of FIG. 5.

Referring to FIG. 6, a transition surface 130 is provided at the boundary between the first profile section 122 and the second profile section 124 and represents a decrease in the cross-section of the bore 116.

Once again, in the second profile section 124 a series of planar surfaces 132 are provided around the internal perimeter of the bore 116, so that in use, the effective transmission of torque between the male and female components is achieved.

Figure 7:
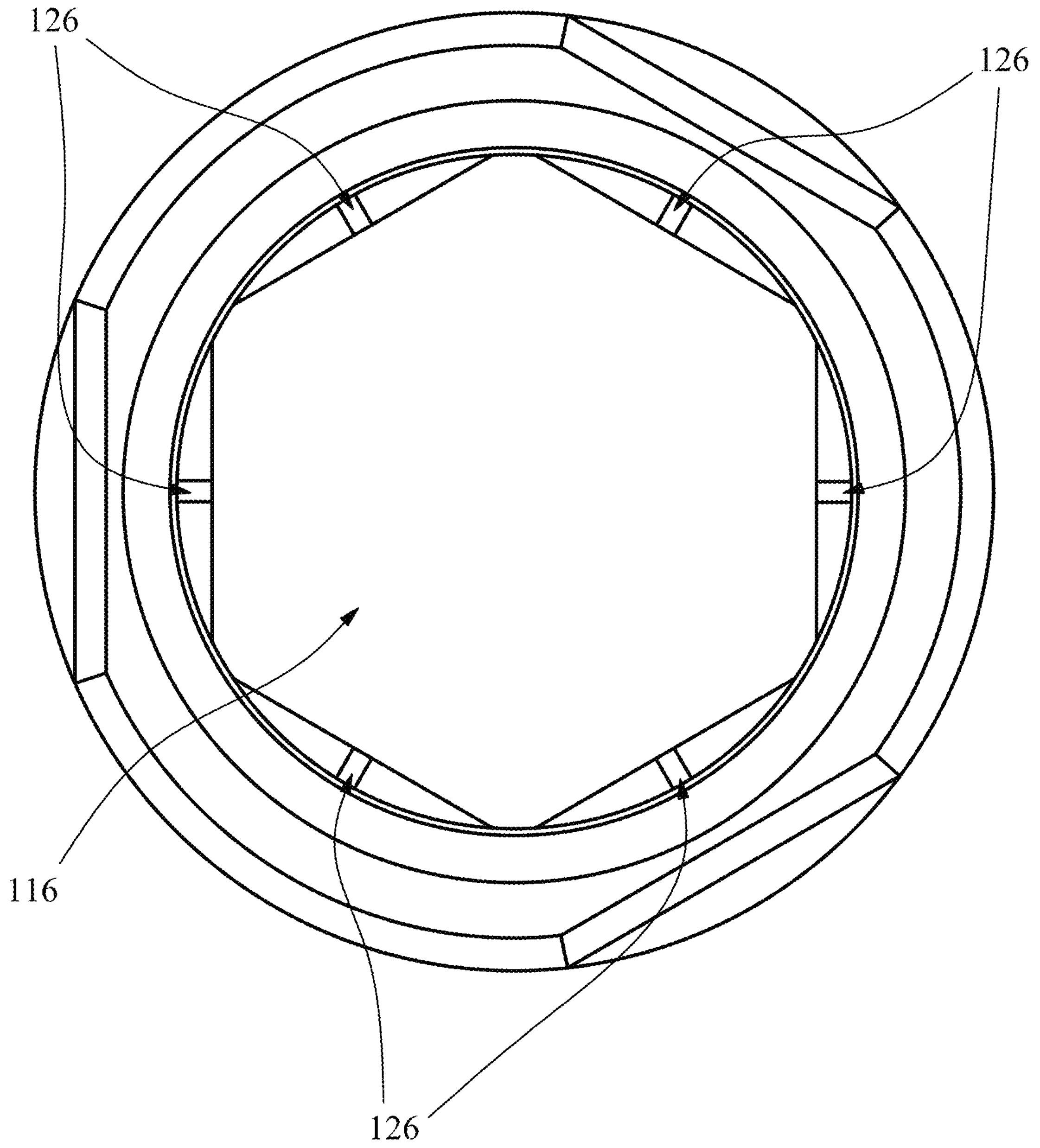
FIG. 7 shows a longitudinal axis view of the female component of FIGS. 5 and 6.
Figure 8B:
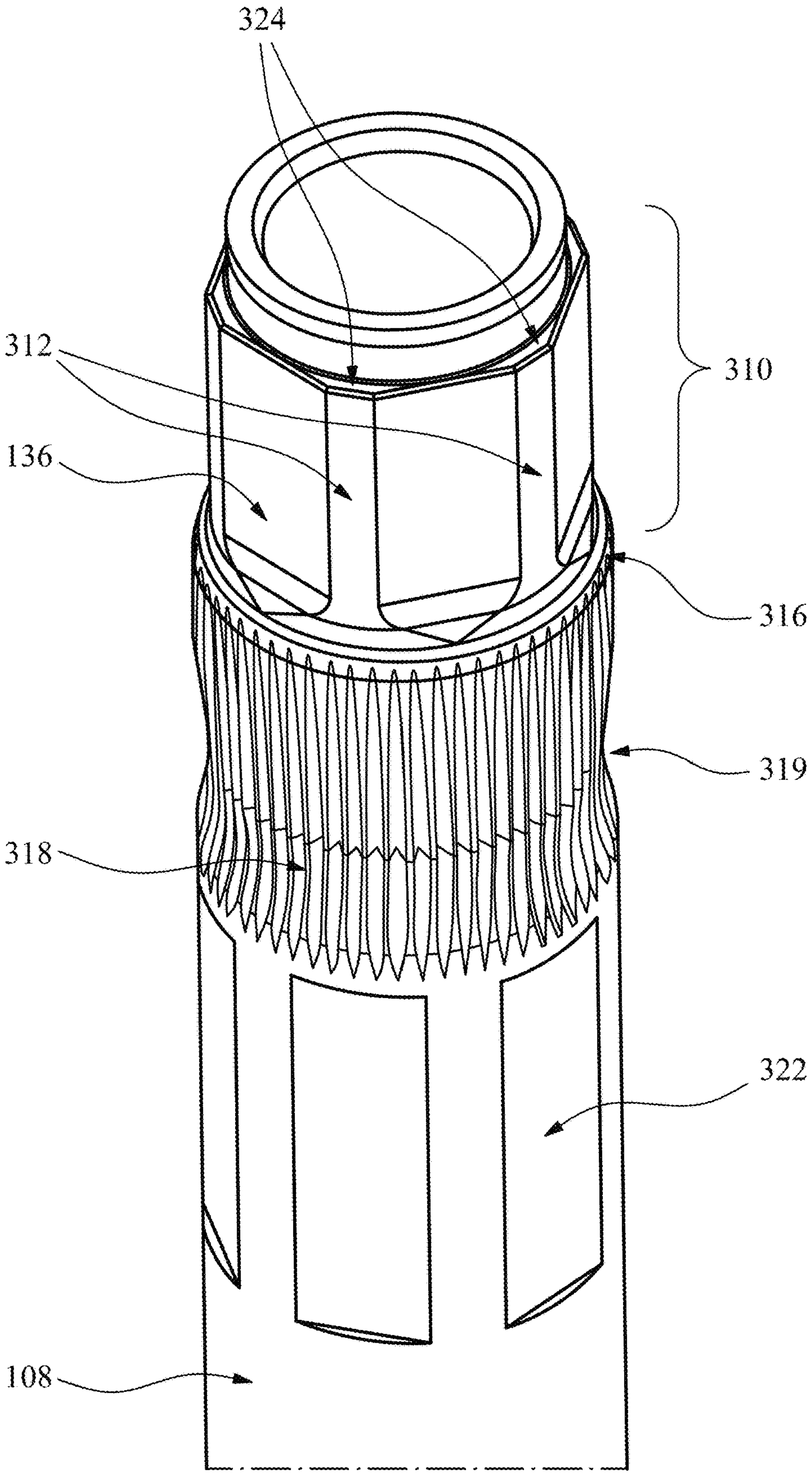
FIG. 8*b* shows the position of the male component of FIG. 8*a* on a surgical procedural element in a further perspective view.
Figure 8C:
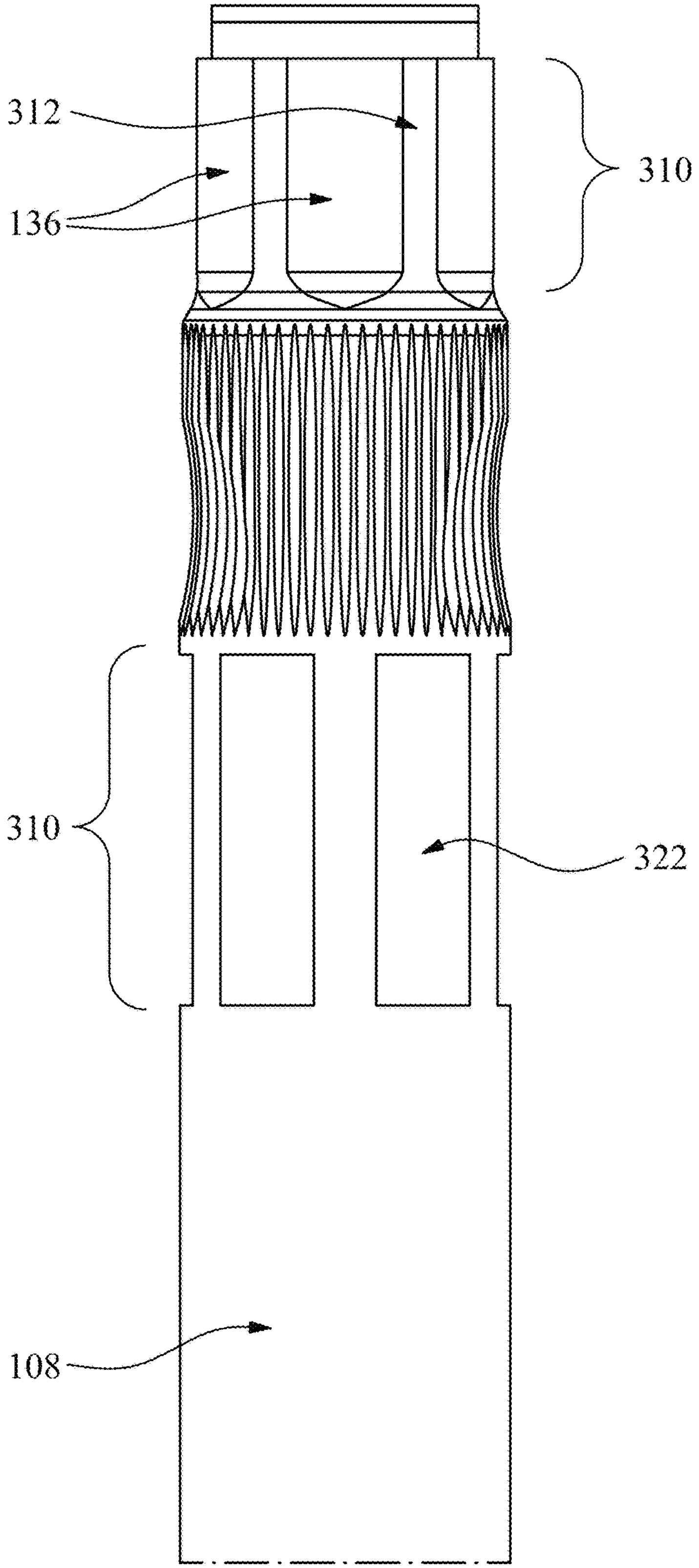
FIG. 8*c* shows the male component and surgical procedural element of FIG. 8*b* in a side view.

As can be seen in FIG. 7, each aligner 126 extends medially into the bore 116 once again. The medial extent of each aligner 126 is configured such as to vary the cross-sectional profile from the circular cross-sectional profile seen at the start 140 of the second profile section 124 to the hexagonal cross-sectional profile seen at further locations 142 into the second profile section 124.

As apparent from a comparison of FIGS. 5 and 6 with FIGS. 2 and 3, in the second embodiment's second profile section 124, the aligners 126 are provided with a different profile. Each aligner 126 is still positioned axially in front of a planar surface 132, considered relative to the insertion of the male component 106 into the female component 100. The aligner 126 still defines a first alignment surface 142 and a second alignment surface 144 with an apex surface 146 provided between them. The apex surface 146 is curved to provide a smooth transition between the first alignment surface 144 and the second alignment surface 144.

The two embodiments differ in terms of the angle of inclination of the first alignment surface 142 and the second alignment surface 144. As can be seen in FIGS. 5 and 6, the angle of inclination is much lower in the second embodiment.

Figure 10B:
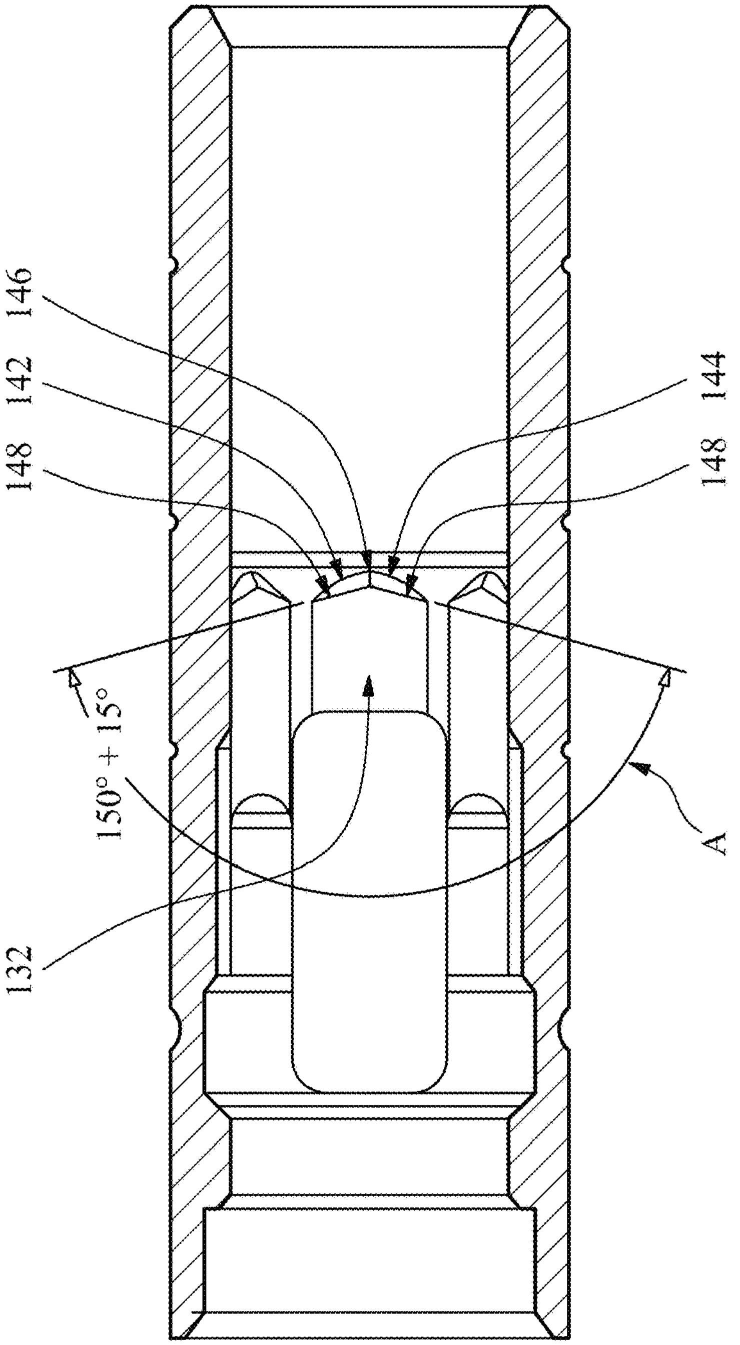
FIG. 10*b* is a cross-sectional view of the further embodiment of FIG. 10*a* on section J-J.
Figure 10A:
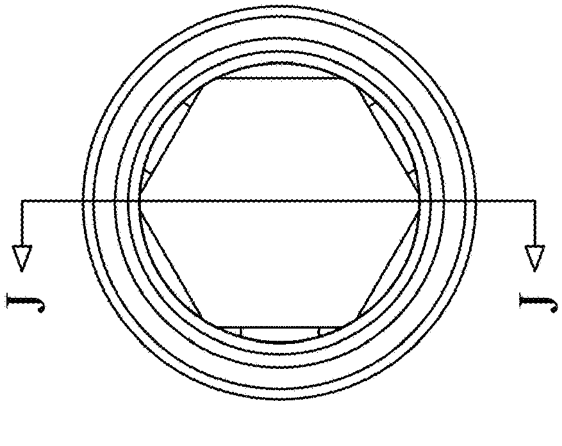
FIG. 10*a* is a longitudinal axis view of a female component in a further embodiment of the disclosure, showing section J-J.

Referring to a further embodiment, as shown in FIGS. 10*a* and 10*b*, the angle of inclination is described in more detail.

Referring to FIG. 10*b*, an angle between the first alignment surface 142, at its medial edge 148, and the second alignment surface 144, at its medial edge 148, is considered. The full angle A between the two is 150°+/−15° in this further embodiment. In effect, this angle A can also be considered to be the apex angle of the planar surface 132 between the two medial edges 148.

Figures 11A, 11B, 11C:
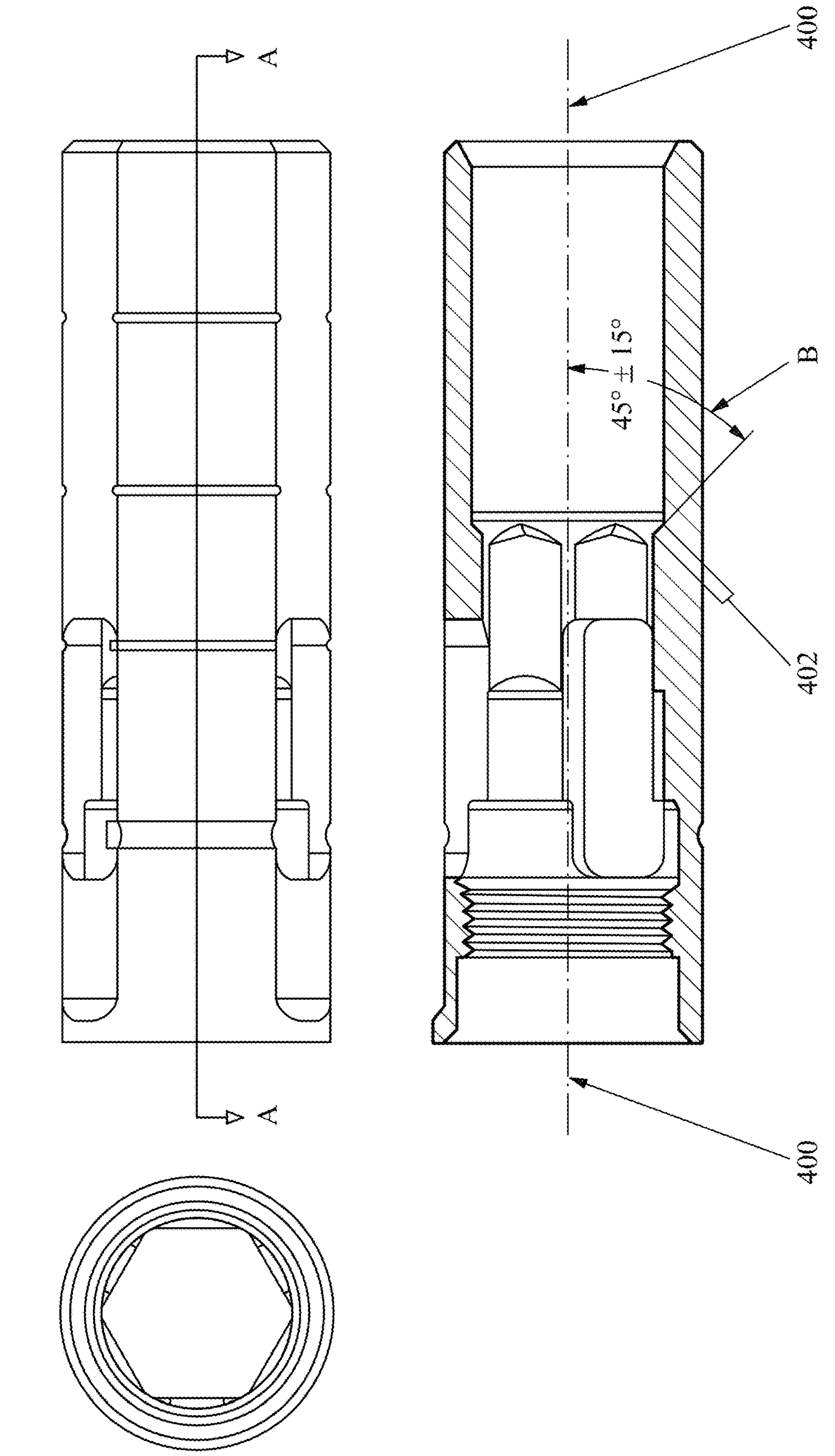
FIG. 11*a* is a longitudinal axis view of the female component in a still further embodiment of the disclosure, showing section A-A
FIG. 11*b* is a cross-sectional view of the female component in the still further embodiment of the disclosure, showing section A-A.
FIG. 11*c* is a cross-sectional view of the still further embodiment of FIGS. 11*a* and 11*b*, on section A-A.

Referring to FIGS. 11*a*, 11*b* and 11*c*, a second angle B is considered. This is the medial slope of the alignment surfaces 142, 144 and/or apex surface 146. This can be defined, as shown in FIG. 11*c*, as the angle between the central axis 400 and the line of inflexion 402 of the apex surface 146. The line of inflexion 402 represents the crest defined by the transition from the first angular direction, for instance of the first alignment surface 142, and the oppositely inclined second angular direction, for instance of the second alignment surface 144. The full angle B between the two is 45°+/−5° in this still further embodiment. The angle B could be similarly defined between the central axis 400 and any line extending across the first alignment surface and/or second alignment surface, where that line is aligned axially with the central axis 400 and/or follows the minimum distance across the alignment surface at that location.

Considering the angle A, the arrangement of the first alignment surface 142 and second alignment surface 144 in the second embodiment [FIGS. 5, 6] and/or further embodiment [FIG. 10*b*] and/or still further embodiment [FIGS. 11*a*, *b* and *c*] means that there is less axial distance of movement involved in rotating the components into alignment than in the first embodiment [FIGS. 2 and 3]. This may give reduced ease of passive rotary alignment due to the application of axial force, as the frictional forces encountered are higher, but the angle is still sufficient to deliver the passive rotary alignment in response to the user applied axial force pushing the female component onto the male component. In this context, passive rotation is rotation caused by the axial force applied, interacting with the profiles of the female and male components, without the user applying any rotational force or actively seeking to rotate to increase alignment. Once aligned, the user applied axial force doesn't cause any further rotation and the female component advances onto the male component axially only.

Overall, the configuration represents a good balance between this aim of passive rotary alignment when the user applies the axial compressive force and the competing aim of providing sufficient engagement area between the female component and the male component for sufficient torque transmission, whilst staying within the female component's maximum permissible size, given the limited space claims that can be made in the operational environment. Materially expanding the size of the female component to allow for larger torque transmission surfaces is not a desirable option in the surgical environments the system is to be used in.

The proportion of the circumference of the bore 116 occupied by the planar surfaces 132 is higher in the second embodiment [FIGS. 5, 6] and/or further embodiment [FIG. 10*b*] and/or still further embodiment [FIGS. 11*a, b* and *c*] than in the first embodiment [FIGS. 2 and 3] and so assists with torque transmission.

Returning to FIG. 5, in one of the three planar sections 112 of the external wall 110, the second embodiment provides for a through aperture 200. The through aperture 200 leads through to the third profile section 128 and allows for visual confirmation of the correct axial insertion of the male component 106 into the female component 100.

Turning to FIG. 8*a*, the male component 106 is provided at the proximal end 300 of a surgical procedural element 108. The male component 106 has an open central bore 302 surrounded by an end face 304 which in the illustrated form is annular. A transition surface 306 extends between the end face 304 and initial element 308 of the engagement section 310 provided by the male component 106. The engagement section 310 is formed by opposing components to those provided on the female component 100. Thus the engagement section 310 provides three planar sections 136 and three part-cylindrical sections 312 intermediate those.

In the proximal most part of the engagement section 310, the male component 106 provides a radially outward tapering surface 314 which receives the aligners 126 when correctly aligned.

Beyond the engagement section 310 in a distal direction, the male component 106 provides a second transition surface 316 which leads to an optional grip section 318. The optional grip section 318 is formed of a series of grooves and ridges. As shown, see FIG. 8*b*, these are axially aligned, but other orientations could be used. In the illustrated embodiment, the grip section 318 has a reduced cross-sectional profile at a location intermediate 319 the two ends of that grip section 318.

The grip section 318 is followed in the distal direction by a second engagement section 320. The secondary engagement section 320 includes a series of flat surfaces 322 which enable the application of torque to the surgical procedural element 108, if needed.

The fully engaged configuration of the female 100 and male component 106 can be seen in FIG. 9.

In operation, the female component 100 and the male component 106 are brought together and the proximal end 300 of the male component 106 enters the bore 116 of the female component 100. The first profile section 122 allows the introduction in any rotational position. The movement in this stage is axial movement only of the female component 10 and male component 106 relative to one another.

Eventually, axial movement of the female component 100 and the male component 106 towards one another, will result in proximal end parts 324 of the part-cylindrical sections 312 within the engagement section 320 of the male component 106, abutting a part of the aligners 126 in the female component 100. The abutment may be with the apex surface 146 of the aligners 126. The form of the apex surface 146 assists in encouraging rotation of any part of the male component 106, most probably the proximal end parts 324, which encounters it first. This rotation occurs passively in response to the axial force applied by the user, due to the shape and configuration employed. This leads to the proximal end parts 324 of the male component 106 contacting one of the first alignment surface 142 or second alignment surface 144 and so provides for further rotation of the male component 106 and female component 100 relative to one another. Continued axial force application causes continued rotation and increasing alignment of the proximal end parts 324 and the part-cylindrical sections 312 more generally of the male component 106 with the gap 152 between the first alignment surface 142 and the second alignment surface 144.

Once aligned rotationally, continued axial only movement of the female component 100 and male component 106 occurs as the slide relative to one another. This in return results in the full extent of axial movement of the female component 100 and male component 106 towards one another and hence results in full alignment and opposition of the set of female engagement surfaces 134 with the set of male engagement surfaces 136.

The aligners 126 configuration results in axial movement of the male component 106 and female component 100 toward one another causing passive rotation and hence alignment of the female engagement surfaces 134 and male engagement surfaces 136. In effect radial passive self-alignment is provided. Both radial locking and rotational locking is thus achieved in a simple and reliable manner. A chamfer alone, for instance, would only achieve axial alignment and not provide any rotational locking.

Whilst achieving these benefits, it can be seen from FIG. 4 in particular, that the approach adds very little material thickness to the design and so is a suitable approach to use in systems that must operate in small spaces, for instance pin drivers.

The incline of the first alignment surface 142 and the second alignment surface 144 can be profiled as needed for the application under consideration. In general, increased inclines for the alignment surfaces will provide for easier alignment; reduced inclines will give greater torque capacity. The application and needs of the surgical procedural element to be operated will guide the appropriate configuration.

In all the embodiment shown, the aligners 126 are configured to provide rotational alignment by relative rotation of the male component 106 and/or female component 100 in either direction. By modifying the profile of the aligners 126, one-directional alignment can be employed. In this format, only a single alignment surface 142 or alignment surface 146, depending upon the directional hand of rotation desired to give alignment, is provided for each aligner 126 and each is inclined in the same direction annularly. The single alignment surface 142, 144 used would be larger than in the illustrated embodiments.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

The invention claimed is:

1. A mounting component for connecting a surgical procedural element to another element, the mounting component comprising:

a. a mount body provided at an end of the another element or at the end of the surgical procedural element; wherein:

i. the mount body has a first end and a second end, the mount body has a longitudinal axis, the first end being spaced from the second end along the longitudinal axis, ii. the mount body has a first surface profile section, the first surface profile section including a first radial profile considered perpendicular to the longitudinal axis;

iii. the mount body has a second surface profile section, the second surface profile section being closer to the second end of the mount body than the first surface profile section, the second surface profile section including a second radial profile considered perpendicular to the longitudinal axis and parallel to the first radial profile;

iv. wherein the second surface profile section is at least partially defined by one or more alignment elements and the second radial profile has a different radial profile to the first radial profile surface due to the presence of the one or more alignment elements;

v. wherein one or more or all, of the alignment elements have a non-constant cross-sectional profile considered along a first part of the longitudinal axis, the first part of the longitudinal axis with the non-constant cross-section being closer to the first surface profile section than a second part of the longitudinal axis where the cross-section is considered;

vi. wherein the non-constant cross-section along a first part of the longitudinal axis defines an alignment element transition part of the second surface profile section and the second surface profile section defines an alignment element transition part; and vii. wherein a first alignment element transition part, such as a first abutment surface, is angled relative to a second alignment element transition part, such as a second abutment surface by an angle that is 150°+/−30°.

2. A mounting component according to claim 1, wherein the second surface profile section has a different radial profile to the first surface profile section surface due to the presence of the one or more alignment elements and the one or more alignment elements reduce the different radial profile in those parts of the second surface profile section for which they are present.

3. A mounting component according to claim 2, wherein the one or more alignment elements extend radially inward.

4. A mounting component according to claim 3, wherein the alignment elements are provided in a regular pattern around the second surface profile section.

5. A mounting component according to claim 4, wherein an intermediate area is provided between two alignment elements within the second surface profile section, the intermediate area being an area where the different radial profile is different to the different radial profile where an alignment element is present.

6. A mounting component according to claim 5, wherein one or more or all, of the alignment elements have the same radial profile as each other.

7. A mounting component according to claim 6, wherein one or more or all, of the alignment elements have a different radial profile at two or more different axial positions.

8. A mounting component according to claim 1, wherein the alignment element transition part provides one or more abutment surfaces for one or more alignment elements.

9. A mounting component according to claim 8, wherein one or more or all, of the alignment element transition parts may include a first abutment surface inclined in one direction and a second abutment surface inclined in a second direction.

10. A mounting component according to claim 1, wherein a first direction of inclination and/or a second direction of inclination of one or more alignment element transition parts includes a component of the incline which is towards the second end of the mount and/or a component axially along the mount body.

11. A mounting component according to claim 1, wherein an alignment element transition part is inclined in a first direction which is anticlockwise about a central axis and/or the another alignment element transition part is inclined in a second direction which is clockwise about a central axis.

12. A mounting component according to claim 1, wherein an alignment element transition part is provided with a further inclination direction inwards relative to the bore and/or towards a central axis.

13. A mounting component according to claim 1, wherein in the transition state, particularly in a first part of the transition state, axial movement of the surgical procedural element and the another element relative to one another is provided without causing relative rotational movement of the surgical procedural element and the another element relative to one another.

14. A mounting component according to claim 13, wherein in the transition state, particularly in a second part of the transition state, axial movement of the surgical procedural element and the another element relative to one another is provided which causes relative rotational movement of the surgical procedural element and the another element relative to one another.

15. A mounting component according to claim 14, wherein in the transition state, particularly in a third part of the transition state, axial movement of the surgical procedural element and the another element relative to one another is provided without causing relative rotational movement of the surgical procedural element and the another element relative to one another.

* * * * *